US012806068B2

(12) United States Patent
Kerth et al.

(10) Patent No.: US 12,806,068 B2
(45) Date of Patent: Nov. 24, 2026

(54) WEARABLE THERAPEUTIC DEVICE WITH REPLACEABLE PADS, AND RELATED SYSTEMS AND METHODS

(71) Applicant: HYPERICE IP SUBCO, LLC, Irvine, CA (US)

(72) Inventors: Trevor Austin Kerth, San Diego, CA (US); Alexander Joseph Aguiar, San Diego, CA (US); Robert Glen Edwards, San Diego, CA (US); Joseph Benjamin Cannon, Long Beach, CA (US)

(73) Assignee: HYPERICE IP SUBCO, LLC, Irvine, CA (US)

( * ) Notice: Subject to any disclaimer, the term of this patent is extended or adjusted under 35 U.S.C. 154(b) by 1085 days.

(21) Appl. No.: 17/733,620

(22) Filed: Apr. 29, 2022

(65) Prior Publication Data

US 2022/0347010 A1 Nov. 3, 2022

Related U.S. Application Data

(60) Provisional application No. 63/182,703, filed on Apr. 30, 2021.

(51) Int. Cl.

*A61F 7/02* (2006.01)
*A61F 7/00* (2006.01)
*A61H 23/02* (2006.01)

(52) U.S. Cl.

CPC ................ *A61F 7/02* (2013.01); *A61F 7/007* (2013.01); *A61H 23/02* (2013.01);

(Continued)

(58) Field of Classification Search

CPC ... A61H 23/00; A61H 23/02; A61F 7/007–02; A61F 2007/0226;

(Continued)

(56) References Cited

U.S. PATENT DOCUMENTS 11,419,753 B2 * 8/2022 Vergara ................. A61F 7/0053
11,771,587 B1 * 10/2023 Maunder ................. A61F 7/007 607/96

(Continued)

FOREIGN PATENT DOCUMENTS

WO WO-2014/113813 A1 7/2014

OTHER PUBLICATIONS

International Search Report and Written Opinion of PCT/US2022/027059 dated Aug. 1, 2022, 13 pages.

*Primary Examiner* — Joseph D. Boecker
*Assistant Examiner* — Thomas W Greig
(74) *Attorney, Agent, or Firm* — Foley & Lardner LLP

(57) ABSTRACT

Systems and methods for providing vibration and temperature therapy via a therapy device is disclosed. According to one embodiment, a therapy device includes a pad comprising an adhesive layer configured to adhere to a skin surface of a user. The therapy device includes a control unit coupled to the pad. The control unit is configured to provide temperature therapy to the skin surface of the user and provide vibration therapy to the skin surface of the user. The pad includes a coupling connector configured to removably couple the control unit. The pad can include a heat generation module comprising a resistive wire and a heat spreader. The pad can include one or more electrical stimulation modules, wherein each electrical stimulation module comprises a conductor and a pad. The pad includes a temperature sensor coupled to the heat generation module. The adhesive layer can be coupled to the heat spreader.

16 Claims, 15 Drawing Sheets

(52) U.S. Cl.
CPC ................. *A61F 2007/0052* (2013.01); *A61F 2007/0226* (2013.01); *A61F 2007/0246* (2013.01); *A61H 2201/5097* (2013.01)

(58) Field of Classification Search
CPC ...... A61F 2007/0071; A61F 2007/0075; A61F 2007/0093; A61F 2007/0094; A61F 2007/0096
See application file for complete search history.

(56) References Cited

U.S. PATENT DOCUMENTS

| | | | | |
|---|---|---|---|---|
| 2006/0241730 | A1* | 10/2006 | Huang | A61F 7/007 607/98 |
| 2010/0228304 | A1* | 9/2010 | Kriksunov | A61F 7/007 607/46 |
| 2012/0046719 | A1* | 2/2012 | Stuffel | A61F 7/007 607/111 |
| 2014/0200487 | A1* | 7/2014 | Ramdas | A61B 5/1075 601/2 |
| 2016/0129274 | A1* | 5/2016 | Park | A61N 1/40 607/3 |
| 2016/0143091 | A1* | 5/2016 | Augustine | A61B 18/16 219/528 |
| 2016/0299543 | A1* | 10/2016 | Brooks | H05B 3/145 |
| 2017/0028196 | A1 | 2/2017 | Stopperan | |
| 2019/0053938 | A1* | 2/2019 | Mandal | A61F 7/007 |
| 2021/0052418 | A1* | 2/2021 | Breiter | A61B 5/395 |

* cited by examiner

WEARABLE THERAPEUTIC DEVICE WITH REPLACEABLE PADS, AND RELATED SYSTEMS AND METHODS

CROSS-REFERENCE TO RELATED APPLICATIONS

This application claims priority to and the benefit of U.S. Provisional Patent Application No. 63/182,703, entitled "WEARABLE THERAPEUTIC DEVICE WITH REPLACEABLE PADS, AND RELATED SYSTEMS AND METHODS," filed on Apr. 30, 2021, the entirety of which is incorporated herein by reference.

TECHNICAL FIELD

The present disclosure relates generally to the physical therapy and/or temperature therapy field, and more specifically a therapy device that provides for vibration, stimulation, and/or heating therapy. The therapy device may include a power and control unit and a replaceable pad.

BACKGROUND

Temperature therapy (e.g., heat therapy), vibration therapy, and electric stimulation therapy have each been shown to be effective in injury recovery, helping to expedite the healing process while reducing pain, inflammation, and joint stiffness. Electric stimulation therapy may include one or more of transcutaneous electrical nerve stimulation ("TENS"), electrical muscle stimulation, neuromuscular stimulation, and neuromodulation therapies. Electric stimulation therapy may operate to apply electrical signals to cell regions of a user, where the applied electrical signals may interact with neurotransmission pathways within the cell regions to alleviate pain, or interact with muscles to promote muscle growth and/or improve muscle tone. Electrical signals may include varying forms of waveforms and pulses that may be applied in controlled sequences at targeted body regions of a user.

The foregoing examples of the related art and limitations therewith are intended to be illustrative and not exclusive, and are not admitted to be "prior art." Other limitations of the related art will become apparent to those of skill in the art upon a reading of the specification and a study of the drawings.

SUMMARY

A system for providing vibration, heating, and/or electrical stimulation therapy via a therapy device is disclosed. According to one embodiment, a therapy device includes a pad including an adhesive layer configured to adhere to a skin surface of a user. The therapy device can include a control unit coupled to the pad and configured to: provide temperature therapy to the skin surface of the user, and provide vibration therapy to the skin surface of the user.

In various embodiments, the therapy device can include one or more of the following features. The control unit can be further configured to: receive one or more control instructions for controlling the temperature therapy and/or the vibration therapy. The control unit can include a wireless connection. The control unit can be further configured to receive the one or more control instructions via the wireless connection. The control unit can include one or more input devices and the control unit can be further configured to receive the one or more control instructions via the one or more input devices. The control unit can include a vibration module configured to provide the vibration therapy. The therapy device can include a coupling mechanism, wherein the pad and the control unit are configured to removably couple via the coupling mechanism. The coupling mechanism can include one or more magnets. The control unit further can include the coupling mechanism and the pad can include a coupling connector configured to removably couple to the coupling mechanism. The pad can include a heat generation module including a resistive wire and a heat spreader, wherein the heat generation module is configured to provide the temperature therapy. The adhesive layer can be disposed on the heat spreader. The control unit can be configured to provide electrical stimulation therapy to the skin surface of the user. The pad can include one or more electrical stimulation modules configured to provide the electrical stimulation therapy, where each electrical stimulation module includes a conductor and a pad. The pad can include a temperature sensor configured to measure a temperature of the temperature therapy.

According to one embodiment, a therapy pad can include a coupling connector configured to removably couple a control unit. The therapy pad can include a heat generation module including a resistive wire and a heat spreader. The therapy pad can include one or more electrical stimulation modules, wherein each electrical stimulation module includes a conductor and a pad. The therapy pad can include a temperature sensor coupled to the heat generation module. The therapy pad can include an adhesive layer coupled to the heat spreader.

According to one embodiment, a method for controlling a therapy device can include receiving, by a control unit of the therapy device, one or more control instructions for controlling a temperature therapy and/or a vibration therapy. The method can include sending, from the control unit to a pad of the therapy device, a subset of the one or more control instructions, wherein the pad includes an adhesive layer configured to adhere to a skin surface of a user, wherein the control unit is coupled to the pad. The method can include receiving, by the pad from the control unit, the subset of the one or more control instructions. The method can include providing, by control unit via the pad, the temperature therapy and/or the vibration therapy to the skin surface of the user based on the one or more control instructions.

The above and other preferred features, including various novel details of implementation and combination of events, will now be more particularly described with reference to the accompanying figures and pointed out in the claims. It will be understood that the particular systems and methods described herein are shown by way of illustration only and not as limitations. As will be understood by those skilled in the art, the principles and features described herein may be employed in various and numerous embodiments without departing from the scope of any of the present inventions. As can be appreciated from the foregoing and the following description, each and every feature described herein, and each and every combination of two or more such features, is included within the scope of the present disclosure provided that the features included in such a combination are not mutually inconsistent. In addition, any feature or combination of features may be specifically excluded from any embodiment of any of the present inventions.

The foregoing Summary, including the description of some embodiments, motivations therefor, and/or advantages thereof, is intended to assist the reader in understanding the present disclosure, and does not in any way limit the scope of any of the claims.

BRIEF DESCRIPTION OF THE DRAWINGS

The accompanying figures, which are included as part of the present specification, illustrate the presently preferred embodiments and together with the general description given above and the detailed description of the preferred embodiments given below serve to explain and teach the principles described herein.

Figure 1A:
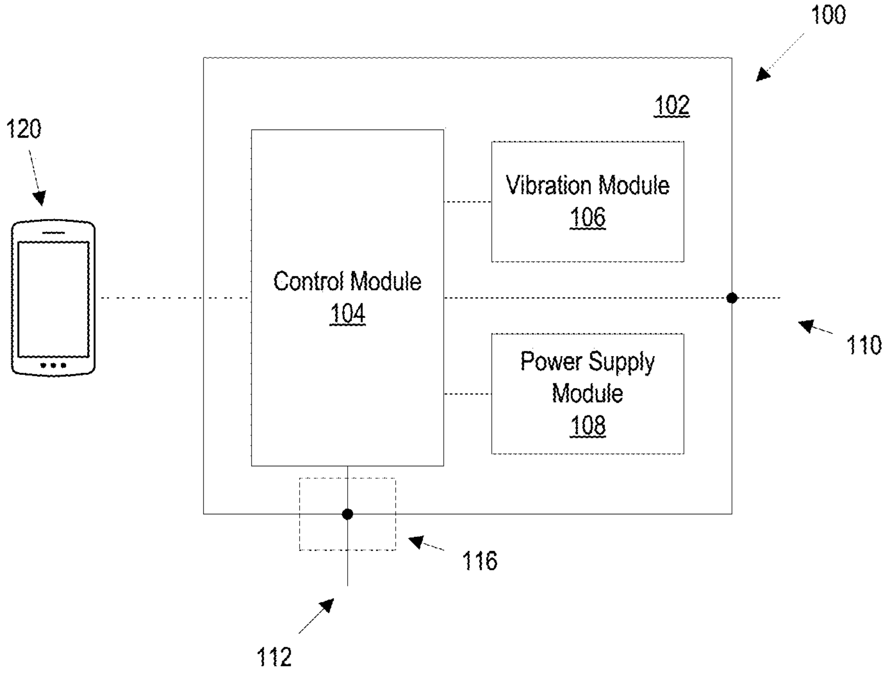
FIG. 1A illustrates a block diagram of an exemplary control unit for an exemplary therapy device, according to some embodiments.

While the present disclosure is subject to various modifications and alternative forms, specific embodiments thereof have been shown by way of example in the drawings and will herein be described in detail. The present disclosure should be understood to not be limited to the particular forms disclosed, but on the contrary, the intention is to cover all modifications, equivalents, and alternatives falling within the spirit and scope of the present disclosure.

DETAILED DESCRIPTION

A system for providing vibration, heating, and/or electrical stimulation therapy via a therapy device is disclosed. It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details.

Overview and Motivation for Some Embodiments

Some therapy devices may provide a combination of heating therapy and vibration therapy to a body region of a user. Such devices may make use of inefficient heating techniques and/or fail to provide targeted, controlled therapy to a body region. In addition, such devices are generally configured for application to a specific body area of a user by way of sleeves, wraps, or straps, such that a user is limited to applying the devices to the specific body areas for which the devices are configured. Further, existing therapy devices may fail to provide a dynamic combination of heating, vibration, and electrical stimulation therapies in a connected device, where the device may be communicatively coupled with one or more other devices to enable customized therapy programs at multiple body regions selected by a user (or a therapy professional). Therefore, use of existing therapy devices may disrupt the required rest/recovery of a user and can contribute to hindering recovery times. Thus, there is a need for improved therapy devices featuring a combination of heating, vibration, and/or electrical stimulation therapies to provide optimized recovery outcomes for a user, while allowing for a modular combination of devices to provide therapy at targeted body regions of the user.

A therapy device can include a control unit and a therapy pad. The control unit can include a power supply module and a control module which can be packaged together in a compact arrangement. In some cases, the control unit can include a vibration device. The therapy pad can include a control receiver module, a thermal modulation system, one or more electrical stimulation modules, and an adhesion layer. The adhesion layer may be configured to couple to a body region of a user. The control unit may couple to the therapy pad via a coupling mechanism. The control module of the control unit may communicate with the control receiver module of the therapy pad to verify the authenticity of the therapy pad.

In some embodiments, the thermal modulation system can include a resistive component, a heat spreader, and a temperature sensor. The temperature sensor can be coupled adjacent and/or proximal to the resistive component and/or the heat spreader to measure temperature (e.g., of the heating therapy) at the therapy pad. In some embodiments, the control module can receive temperature measurement information from the temperature sensor and can control a voltage applied to the resistive component for heating therapy. Based on received control instructions and the temperature measurement information, the control module can drive the resistive component to a target temperature.

In some embodiments, the control module may apply a voltage to the vibration device to provide vibration therapy. An electrical stimulation module may include a conductive layer and a conductive contact. The control module may apply a voltage to the one or more electrical stimulation modules to provide electrical stimulation therapy.

Overview of a Control Unit for a Therapy Device

Referring to FIG. 1A, a block diagram of a control unit 100 of a therapy device is presented, according to some embodiments. In some embodiments, the control unit 100 can include a housing 102, a control module 104 retained by the housing 102, and a power supply module 108 electrically coupled to the control module 104 and retained by the housing 102. In some embodiments, the housing 102 may be made of plastic, alone or in combination with one or more other materials (e.g., silicone). In an example, the plastic may comprise acrylonitrile butadiene styrene (ABS). In some embodiments, the control unit 100 includes a vibration module 106. The vibration module 106 may be coupled to the control module 104. In some embodiments, the control module 104 may be communicatively coupled to a client application executing at a computing device 120 (e.g., a mobile computing device) and to a therapy pad (not shown in FIG. 1A) as described herein. In some embodiments, the control module 104 and the power supply module 108 are combined into a combined control and power supply module.

The power supply module 108 may provide power to the control unit 100 and a therapy pad as described herein. In an example, the power supply module 108 may include a rechargeable energy storage device (e.g., a lithium polymer (LiPo) battery). In some embodiments, the control unit 100 may include one or more input/output (I/O) channels. The control module 104 and/or the power supply module 108 may be coupled to an I/O interface 110. In some embodiments, the I/O interface 110 may serve to communicate information between the control module 104 and one or more computing devices (e.g., the computing device 120). In an example, the I/O interface 110 may support communication via a Universal Serial Bus Type-C (USB-C) connection. In some embodiments, the I/O interface 110 may provide power to the power supply module 108 via the control module 104. In an example, power supplied via a USB-C connect at the I/O interface 110 may charge a rechargeable battery of the power supply module 108. Some non-limiting embodiments of the power supply module 108 are described in further detail below.

In some embodiments the control module 104 may be coupled to a pad interface 112. The pad interface 112 may communicate information between the control module 104 and a therapy pad as described herein. The pad interface 112 may include a plurality of pins (e.g., pogo pins) to provide a communicative and/or electrical connection between the control module 104 and a therapy pad. In some embodiments, the control unit 100 can include a coupling mechanism 116. The coupling mechanism 116 may provide a physical medium to couple the control unit 100 to a therapy pad as described herein. In some embodiments, the coupling mechanism 116 may include one or more magnets, such that the coupling mechanism 116 may couple the control unit 100 to a therapy pad via magnetic force. In some cases, the coupling mechanism 116 may include one or more physical connectors used to couple the control unit 100 to a therapy pad. For example, the coupling mechanism 116 may include one or more snap connectors to couple the control unit to a therapy pad.

Figure 1B:
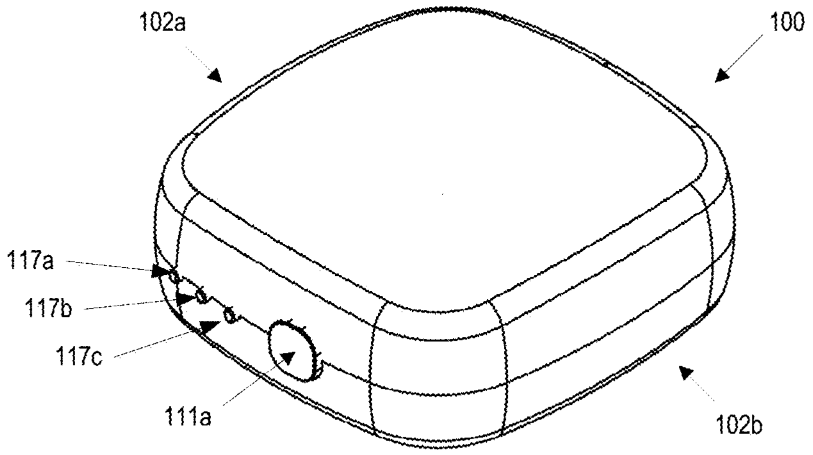
FIG. 1B illustrates a top view of the exemplary control unit for the exemplary therapy device, according to some embodiments.

Referring to FIG. 1B, a top view of a control unit 100 for a therapy device is presented, according to some embodiments. As shown, the control unit 100 can include a housing 102. The housing 102 may have one or more sections. As shown in FIG. 1B, the housing 102 may include a top housing 102*a* and a bottom housing 102*b*. The top housing 102*a* may be made of plastic, alone or in combination with one or more other materials (e.g., silicone). The bottom housing 102*b* may be made of plastic, alone or in combination with one or more other materials (e.g., silicone). In some embodiments, the top housing 102*a* and/or the bottom housing 102*b* may include a silicone layer. The silicone layer may be an exterior layer of the top housing 102*a* and/or the bottom housing 102*b*, where an interior layer of the top housing 102*a* and/or the bottom housing 102*b* is made of plastic as described herein. In some embodiments, the top housing 102*a* and/or the bottom housing 102*b* may include one or more indicators (e.g., 117*a*-117*c*). The one or more indicators may be made of acrylic, where the acrylic is transparent. The one or more indicators may each include a light emitting diode (LED). Each LED may be coupled to the control module 104. The control module 104 may control each LED to activate and/or deactivate each LED. The top housing 102*a* and the bottom housing 102*b* may be coupled together to form the housing 102 and enclose one or more elements of the control unit 100 as described herein with respect to FIG. 1A. In some embodiments, the control unit 100 may include one or more input devices 111. The one or more input devices may be made of silicone. As shown in FIG. 1B, the control unit 100 may include an input device 111*a*. The input device 111*a* may be a push button. The input device 111*a* may be communicatively coupled to the control module 104 such that an input to the control unit 100 may be provided via the input device 111*a*.

Figure 1C:
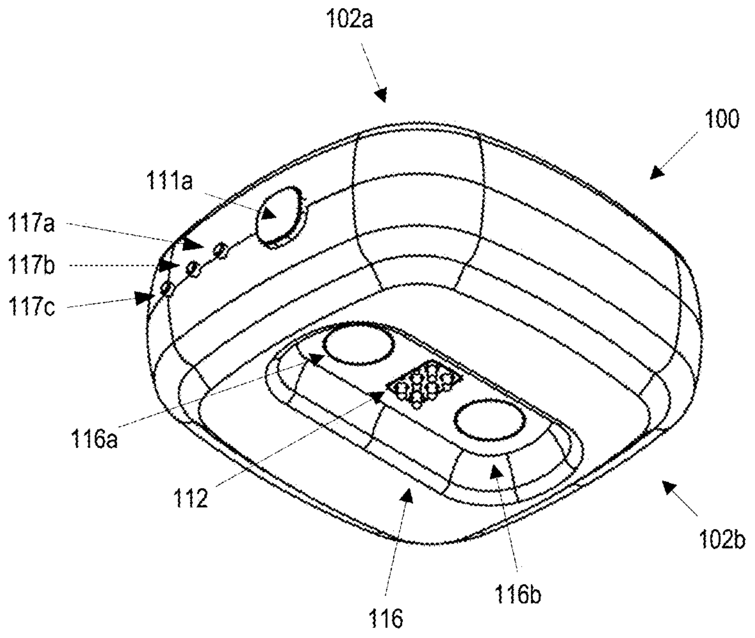
FIG. 1C illustrates a bottom view of the exemplary control unit for the exemplary therapy device, according to some embodiments.

Referring to FIG. 1C, a bottom view of the control unit 100 for a therapy device is presented, according to some embodiments. As shown, the bottom housing 102*b* of the control unit 100 may include a coupling mechanism 116 and a pad interface 112. As discussed above, the coupling mechanism 116 may include one or more magnets to physically couple the control unit 100 to a therapy pad. In the example of FIG. 1C, the coupling mechanism 116 includes magnets 116*a* and 116*b* to couple the control unit 100 to a therapy pad. The magnets 116*a* and 116*b* may each be coupled to the bottom housing 102*b* via an adhesive as described further below. In some cases, the coupling mechanism 116 includes the pad interface 112. As discussed above, the pad interface 112 may have one or more pins, such that the I/O channel may electrically and/or communicatively couple to a therapy pad. The pins of the pad interface 112 may be any type of pin suitable for electrical and/or communicative coupling including, without limitation, spring-loaded pins (or "pogo pins").

Figure 1D:
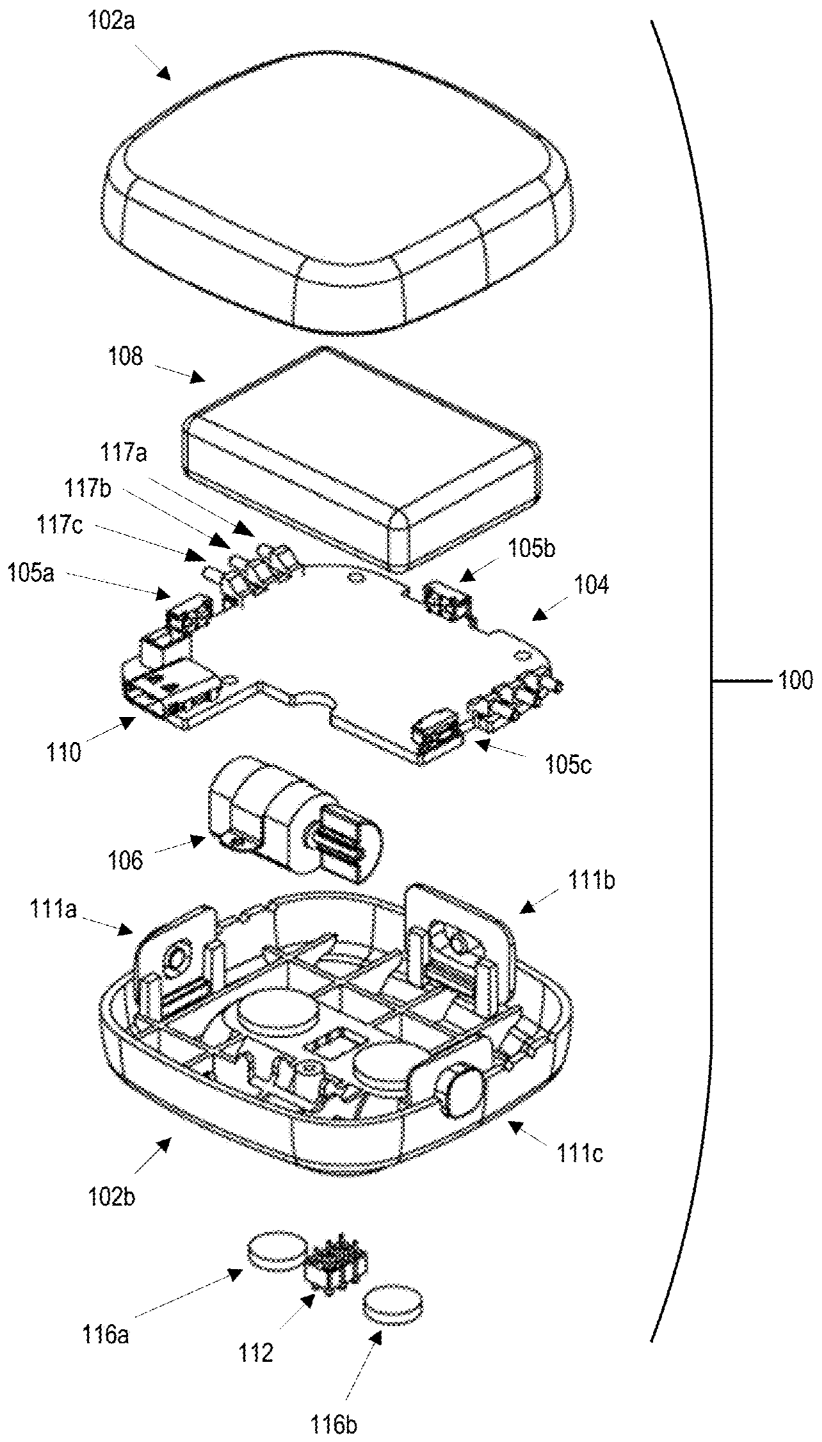
FIG. 1D illustrates an exploded view of the exemplary control unit for the exemplary therapy device, according to some embodiments.

Referring to FIG. 1D, an exploded view of the control unit 100 for a therapy device is presented, according to some embodiments. As shown in FIG. 1D, the control unit 100 may include a plurality of elements. The control unit 100 may include a top housing 102*a*. In some embodiments, the control unit 100 includes a vibration module 106 and a power supply module 108. The vibration module 106 may be positioned adjacent to the power supply module 108. In some embodiments, the vibration module 106 may be a motor (e.g., a coin cell vibration motor). The top housing 102*a* may be positioned above the vibration module 106 and the power supply module 108. In some embodiments, the top housing 102*a* may be positioned flush against the vibration module 106 and the power supply module 108.

In some embodiments, the control unit 100 may include a control module 104. The control module 104 may include a substrate (e.g., a printed circuit board (PCB)) on which one or more other components of the control unit 100 are coupled and/or otherwise mounted. The other components of the control unit 100 may be electrically, communicatively, and/or physically coupled to the substrate of the control module 104. The control module 104 may include a processor, memory, and/or a communications module (not shown in FIG. 1D). The processor may communicate with and/or otherwise control other components of the control unit 100 and/or components of a therapy pad. The processor may communicate with therapy pad via a pad interface 112.

The processor may communicate with a computing device 120 via the I/O channel 110. The control module 104 may be coupled to an I/O interface 110. In some embodiments, the control module 104 may be positioned below the vibration module 106 and the power supply module 108.

In some embodiments, the control module 104 can include one or more connectors 105. The one or more connectors 105 may include connectors 105*a*, 105*b*, and 105*c* as shown in FIG. 1D. The one or more connectors 105 may be physically and/or electrically coupled to the control module 104. In some embodiments, as described herein, the control unit 100 may include one or more input devices 111. As shown in FIG. 1D, the control unit may include input devices 111*a*, 111*b*, and 111*c*. The one or more input devices 111 may be positioned adjacent and/or proximal to the one or more connectors 105, such that the one or more input devices 111 may provide input(s) to the control module 104 via the one or more connectors 105. For example, based on pressing the input device 111*a*, the connector 105*a* may receive an input from the input device 111*a* that may be communicated to the control module 104. The connectors 105*a*, 105*b*, and 105*c* may be physically coupled to the input devices 111*a*, 111*b*, and 111*c* respectively.

In some embodiments, the control unit 100 includes a bottom housing 102*b*. The bottom housing 102*b* may be positioned below the control module 104. The bottom housing 102*b* may couple to the top housing 102*a*, such that the elements of the control unit 100 are enclosed by the top housing 102*a* and the bottom housing 102*b*. In some embodiments, the top housing 102*a* and the bottom housing 102*b* may include an opening, such that the I/O interface 110 may receive connections (e.g., USB-C connections) from one or more connectors.

In some embodiments, the top housing 102*a* and the bottom housing 102*b* may be physically coupled via a coupling mechanism, such that the top housing 102*a* and the bottom housing 102*b* form an enclosure as the control unit 100. In some cases, the coupling mechanism may be one or more connectors (e.g., snap connectors) located on the interiors of the top housing 102*a* and the bottom housing 102*b*. In some cases, the coupling mechanism may include one or more screws, pins, brackets, and/or another other suitable physical coupling mechanism.

In some embodiments, the control unit 100 includes a pad interface 112 as described herein. The pad interface 112 may include one or more pins (e.g., pogo pins) to provide electrical and/or communicative coupling to an external device. In some embodiments, the one or more pins of the pad interface 112 may couple to a mating plate and an I/O channel of a therapy pad as described herein. As shown in FIG. 1D, as an example, the pad interface 112 may include six pins. In some embodiments, the pad interface 112 may include fewer pins (e.g., 2-5 pins) or more pins (e.g., 7-12 pins or more). Some non-limiting examples of techniques for using the pins to electrically and/or communicatively couple the control unit 100 with specific components of a therapy pad 200 are described in further detail below. In some embodiments, the bottom housing 102*b* may include an opening such that the pad interface 112 may protrude and/or otherwise be exposed from the bottom housing 102*b*.

In some embodiments, the control unit 100 includes a coupling mechanism 116. The coupling mechanism 116 may include one or more magnets to physically couple the control unit 100 to a therapy pad.

Overview of a Therapy Pad for a Therapy Device

Figure 2A:
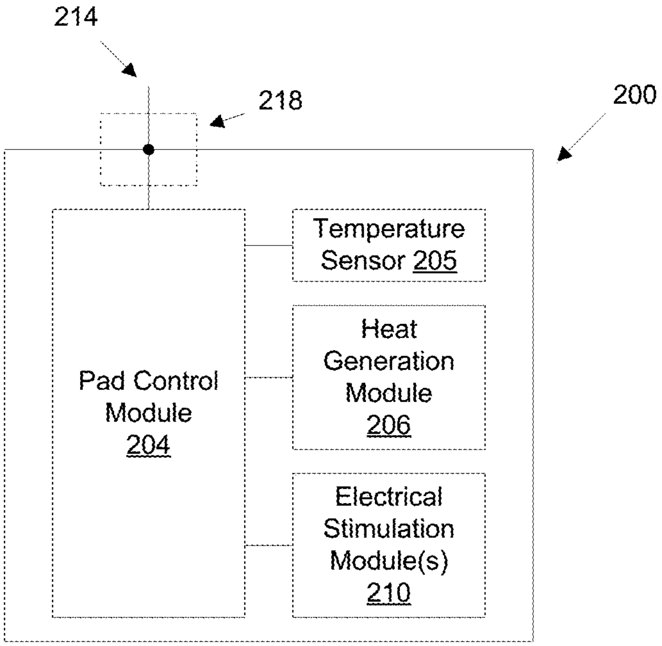
FIG. 2A illustrates a block diagram of an exemplary therapy pad for the exemplary therapy device, according to some embodiments.

Referring to FIG. 2A, a block diagram of a therapy pad 200 of a therapy device is presented, according to some embodiments. In some embodiments, the therapy pad 200 includes a pad control module 204, a temperature sensor 205, and a heat generation module 206. Optionally, some embodiments of the therapy pad 200 include one or more electrical stimulation modules 210.

The heat generation module 206 may generate heat, thereby controlling the temperature of a surface of the therapy pad 200. The temperature sensor 205 may be physically coupled to the heat generation module 206, such that the temperature sensor 205 may measure the temperature at the heat generation module 206. The one or more electrical stimulation modules 210 may provide electrical stimulation. In an example, the therapy pad 200 may include two electrical stimulation modules 210. The one or more electrical stimulation modules 210 may provide transcutaneous electrical nerve stimulation (TENS) to a body region of a user of the therapy pad 200 (and corresponding therapy device) as to be described herein.

In some embodiments, the pad control module 204 may be communicatively and/or electrically coupled to the temperature sensor 205, the heat generation module 206, and the one or more electrical stimulation modules 210. The pad control module 204 may include a processor and/or a memory (not shown in FIG. 2A). The processor may encrypt the memory of the pad control module 204. A processor and/or a memory of the pad control module 204 may be coupled to an I/O channel 214 to communicate with the control module 104 as described herein. In some embodiments, a processor of the pad control module 204 may be communicatively coupled to the temperature sensor 205, the heat generation module 206, and the one or more electrical stimulation modules 210. In an example, the pad control module 204 may be coupled to the I/O channel via one or more electrical conductors (e.g., wires) and removably couplable connectors. The heat generation module 206 may receive temperature control instructions from the pad control module 204. In some cases, the pad control module 204 may receive an indication of the measured temperature of the heat generation module 206 from the temperature sensor 205. In some cases, the pad control module 204 may not be communicatively and/or electrically coupled to the temperature sensor 205, the heat generation module 206, and the one or more electrical stimulation modules 210 (not shown in FIG. 2A), such that the temperature sensor 205, the heat generation module 206, and the one or more electrical stimulation modules 210 are coupled to the control module 104 via an I/O channel 214 as described herein.

In some embodiments, the therapy pad 200 may include an I/O channel 214. The I/O channel 214 may be coupled to the pad control module 204. The I/O channel 214 may include one or more pins (e.g., pogo pins) and/or a connector configured to mate with the pins of the pad interface 112 of the control module 104 to provide a communicative and/or electrical connection between the therapy pad 200 and the control module 104 of the control unit 100. Via the I/O channel 214, the pad control module 204 may communicate information to the control module 104 and the corresponding control unit 100. The pad control module 204 may receive control instructions via the I/O channel 214 for the heat generation module 206 and/or the one or more electrical stimulation modules 210 as to be described herein. In some embodiments, the I/O channel 214 may be coupled to the temperature sensor 205, the heat generation module 206, and/or the electrical stimulation module(s) 210. The control module 104 of the control unit 100 may communicate (e.g., directly communicate) with the temperature sensor 205, the heat generation module 206, and/or the electrical stimulation module(s) 210 via the I/O channel 214. In an example, if the pad interface 112 and the I/O channel 214 are coupled, the control module 104 may communicate directly with each of the temperature sensor 205, the heat generation module 206, and the electrical stimulation module(s) 210 via a number of dedicated pins of the pad interface 112.

In some embodiments, the therapy pad 200 includes a coupling mechanism 218. The coupling mechanism 218 may include the I/O channel 214. The coupling mechanism 218 may provide a physical medium to couple the therapy pad 200 to the control unit 100. In some embodiments, the coupling mechanism 218 may be a "mating plate" based on the positioning of the coupling mechanism 218 and coupling mechanism 116 when physically coupled (e.g., male to female coupling, female to male coupling, etc.). In some embodiments, the coupling mechanism 218 may include one or more magnetic materials such that the coupling mechanism 218 may be coupled to the coupling mechanism 116 (e.g., the magnets 116*a* and 116*b*) of the control unit 100 via magnetic force. In some embodiments, the coupling mechanism 116 and the coupling mechanism 218 may be coupled via alternative methods. Alternative methods may include an adhesive coupling mechanism, a mechanical coupling mechanism (e.g., brackets, screws, tabs, connectors, etc.), etc.

Figure 2B:
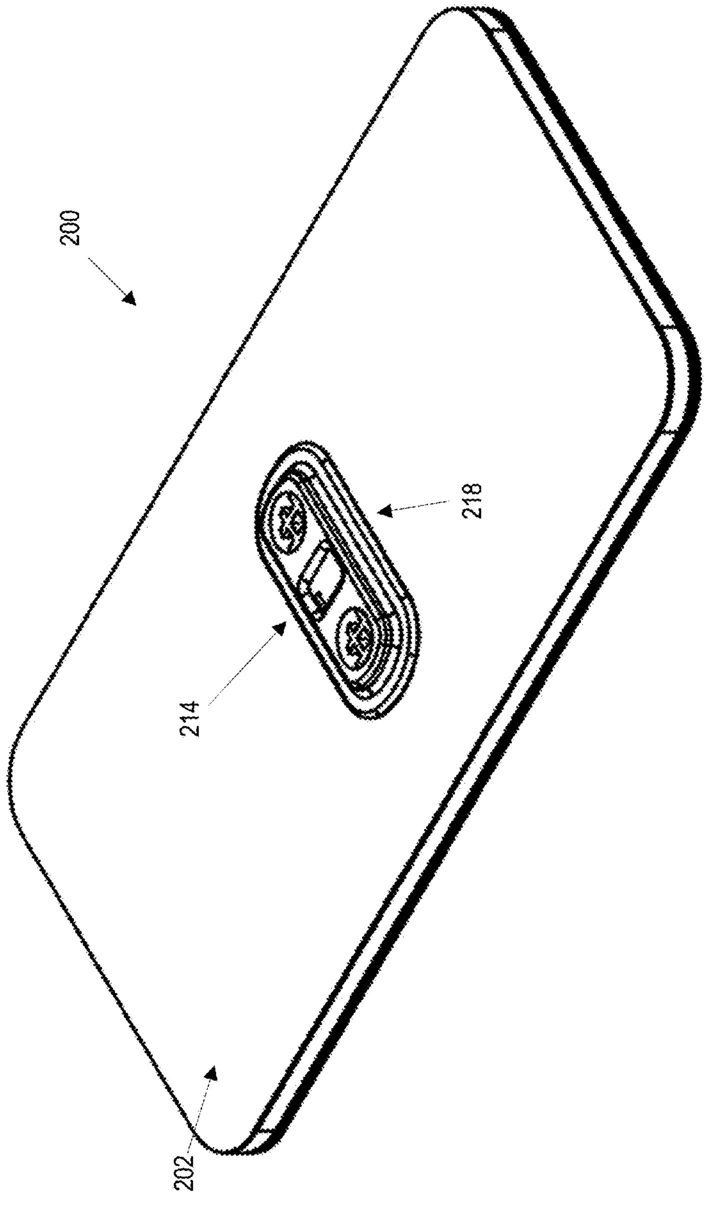
FIG. 2B illustrates a top view of an exemplary therapy pad for the exemplary therapy device, according to some embodiments.

Referring to FIG. 2B, a top view of a therapy pad 200 for a therapy device is presented, according to some embodiments. As shown in FIG. 2B, the therapy pad 200 can include a coupling mechanism 218. The coupling mechanism 218 may include an opening for the I/O channel 214 as described herein, where the I/O channel 214 may include one or more pins (e.g., pogo pins) and/or a connector to receive the one or more pins of the pad interface 112. In some embodiments, the therapy pad 200 can include a top layer 202. The top layer 202 may be positioned below the coupling mechanism 218. The top layer 202 may be made of any suitable material (e.g., any suitable fabric).

Figure 2C:
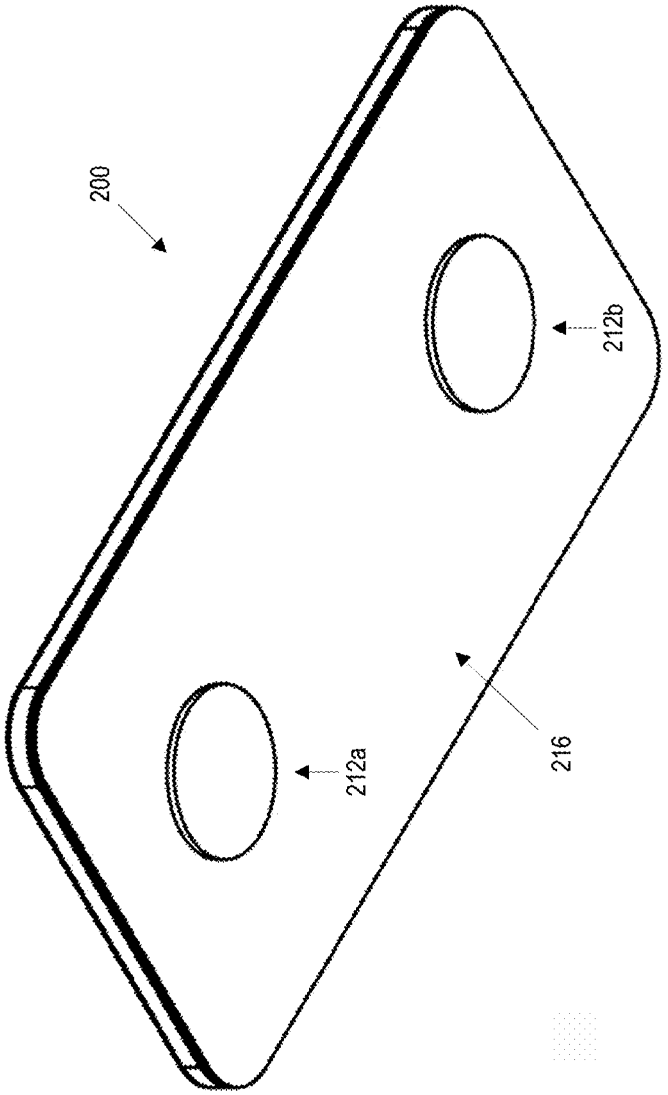
FIG. 2C illustrates a bottom view of an exemplary therapy pad for the exemplary therapy device, according to some embodiments.

Referring to FIG. 2C, a bottom view of the therapy pad 200 for a therapy device is presented, according to some embodiments. In some embodiments, the therapy pad 200 may include one or more pads 212 as part of the one or more electrical stimulation modules 210. Via the pads 212*a* and 212*b*, the electrical stimulation modules 210 may administer electrical stimulation therapy to a user. The surface of each pad 212 may include or be coated by a hydrogel that may conduct an electrical signal and adhere to a body region of user (e.g., to a skin region of a user). In some embodiments, the hydrogel may include a menthol additive, which may soothe irritation at the body region to which the pads 212 are applied.

In some embodiments, the therapy pad 200 may include an adhesive layer 216. The adhesive layer 216 may include an adhesive (e.g., a silicone-based adhesive) that may removably adhere to a body region of a user. For example, the therapy pad 200 may be adhered to the skin of a user via the adhesive layer 216. In some embodiments, the adhesive layer 216 may be reusable to adhere the therapy pad (and corresponding therapy device) to a user to repeatedly provide therapy as described herein. The adhesive layer 216 may be thermally conductive such that heat generated by the heat generation module 206 may be conducted by the adhesive layer 216.

Figure 2D:
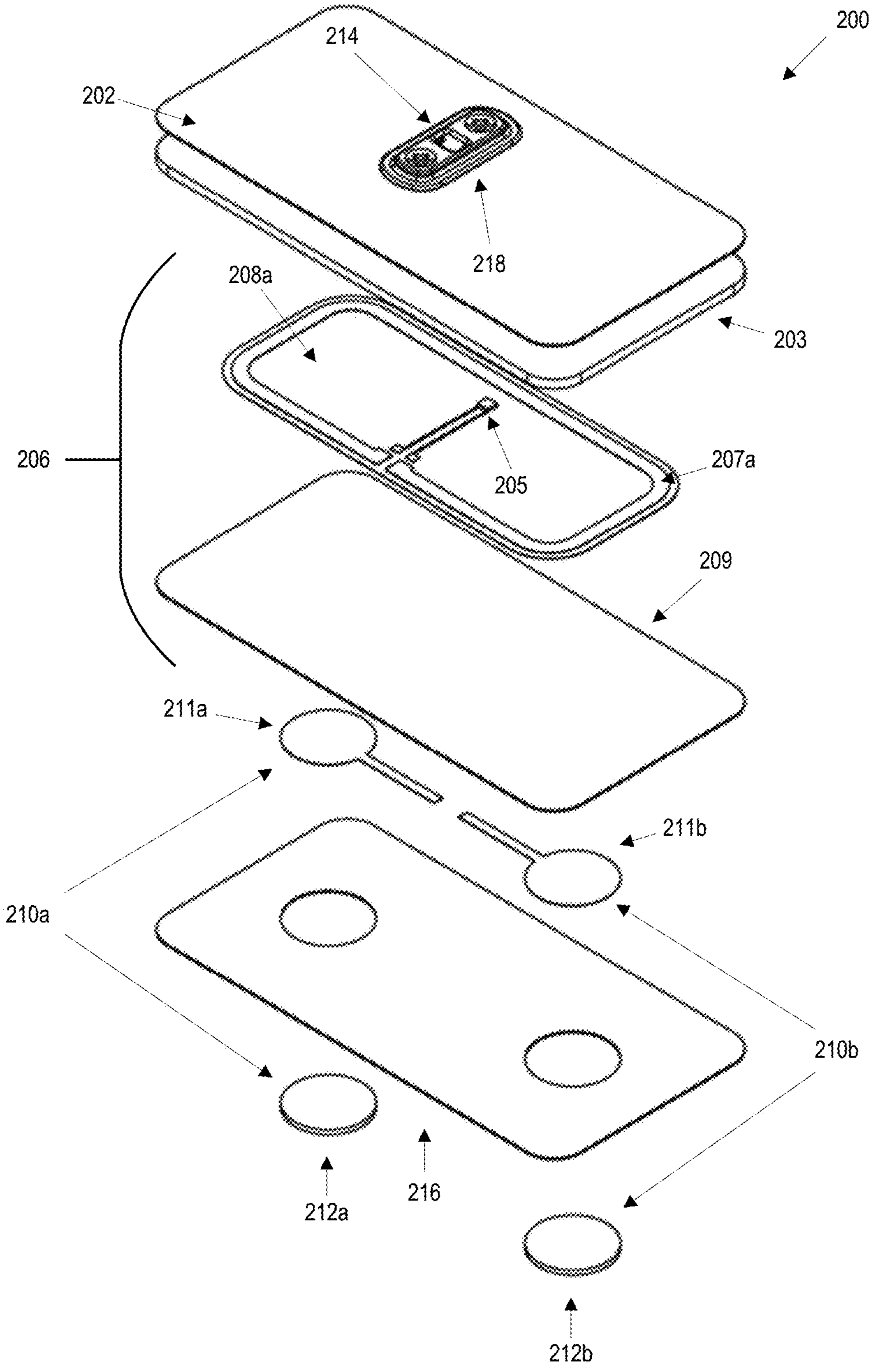
FIG. 2D illustrates an exploded view of an exemplary therapy pad for the exemplary therapy device, according to some embodiments.

Referring to FIG. 2D, an exploded view of the therapy pad 200 for a therapy device is presented, according to some embodiments. As shown in FIG. 2D, the therapy pad 200 may include a plurality of elements. The therapy pad 200 may include a top layer 202. The top layer 202 may be made of a fabric, nylon, vinyl, and/or plastic material as described herein. In some embodiments, the coupling mechanism 218 may be positioned above the top layer 202. The coupling mechanism 218 may include the I/O channel 214 as described herein. In some embodiments, the therapy pad 200 may include an insulator 203. The insulator 203 may be positioned below the top layer 202. The insulator 203 may insulate the top layer 202 from the heat generated by the heat generation module 206. The insulator may be made of neoprene. In an example, the insulator 203 may be a 1.6 mm neoprene layer.

The pad control module 204 (not shown in FIG. 2D) may be positioned at any suitable location on or within the therapy pad 200. In some embodiments, the pad control module 204 (not shown in FIG. 2D) may be positioned above the insulator 203 and below the top layer 202. In some embodiments, the pad control module 204 may be located adjacent to the I/O channel 214 and/or the coupling mechanism 218.

In some embodiments, the therapy pad 200 may include a heat generation module 206. The heat generation module 206 may include a resistive component 207 (referred to in exemplary embodiments as "resistive component 207*a*" or "resistive component 207*b*"), a backing layer 208 (referred to in exemplary embodiments as "backing layer 208*a*" or "backing layer 208*b*"), and a heat spreader 209. In some cases, the resistive component 207 may be and/or include a resistive wire. The control module 104 or pad control module 204 may apply a control voltage to the resistive component 207 to heat the resistive component 207 to a target temperature. In some embodiments, the resistive component 207 may be formed (e.g., printed) directly on the backing layer 208, such that the resistive component 207 and the backing layer 208 are integrated. The backing layer 208 may be made of plastic. In an example, the plastic may be polyamide, polyethylene (PE), or polytetrafluoroethylene (PTFE). In some embodiments, the resistive component 207 may be formed separately from the backing layer 208. The resistive component 207 may be positioned below the insulator 203 and above the backing layer 208. The heat spreader 209 may be positioned below the backing layer 208. The heat spreader 209 may distribute thermal energy generated by the resistive component 207 across an area (e.g., surface) of the heat spreader 209. In some embodiments, the heat generation module 206 may not include the backing layer 208, such that the resistive component 207 may be coupled (e.g., directly attached) to the heat spreader 209.

Figure 2E:
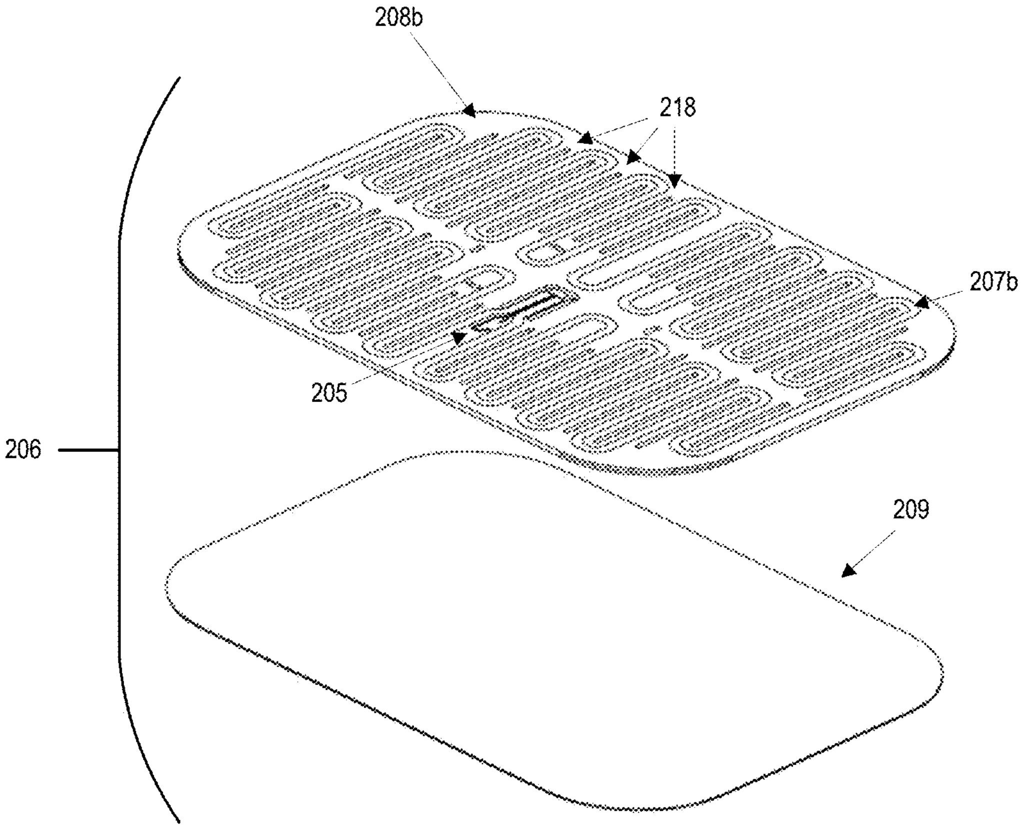
FIG. 2E illustrates a top view of part of an exemplary heat generation module for the exemplary therapy device, according to some embodiments.

In some cases, the resistive component 207 may include one or more embodiments. For example, as shown in FIG. 2D, the heat generation module 206 may include a resistive component 207*a*. As another example, as shown in FIG. 2E, the heat generation module 206 may include a resistive component 207*b*. In some cases, the backing layer 208 may include one or more embodiments. For example, as shown in FIG. 2D, the heat generation module 206 may include a backing layer 208*a*. As another example, as shown in FIG. 2E, the heat generation module 206 may include a resistive component backing layer 208*b*.

The heat spreader 209 may include a top layer, a middle layer, and a bottom layer. In some embodiments, the top layer can include a PET (polyethylene terephthalate) layer, the middle layer can include a graphite/graphene layer, and the bottom layer can include another PET layer. In an example, the middle layer can include a graphene layer which includes a synthetic graphite sheet. In another example, the middle layer can include small particles (e.g., of graphene). In some embodiments, the graphene layer can include a metal based powder for thermal energy transfer. In an example, the middle layer of the heat spreader 209 may include a DSN5050-10DC10SB Synthetic Graphite Sheet from DASEN company.

In some embodiments, the therapy pad 200 may include a temperature sensor 205 as described herein. The temperature sensor 205 may be physically coupled to any one of: the resistive component 207, the backing layer 208, or the heat spreader 209. As shown in FIG. 2D, the temperature sensor 205 may be physically coupled to the backing layer 208. Alternative positioning of the temperature sensor 205 may be used. The temperature sensor 205 may be positioned below the insulator 203 and above the backing layer 208, while positioned proximal to the resistive component 207. For example, as shown in FIG. 2D, the temperature sensor 205 may be disposed between the insulator 203 and above the backing layer 208*a*. The temperature sensor 205 may be communicatively coupled to the control module 104 or pad control module 204 as described herein to communicate temperature data indicative of the temperature of the heat generation module 206. In some embodiments, the temperature sensor 205 may be coupled to (e.g., disposed on) the adhesive layer 216, such that the temperature sensor 205 may be positioned adjacent or proximal to a body region of a user during use of the therapy device. The temperature sensor 205 may be coupled to (e.g., disposed on) the exterior of the adhesive layer 216. In an example, the temperature sensor 205 may be coupled to the exterior of the adhesive layer 216 and therapy pad 200 such that the temperature sensor is adjacent to a user's skin when the therapy device 300 is adhered to the user.

In some embodiments, the therapy pad 200 may include one or more electrical stimulation modules 210. In some embodiments, an electrical stimulation module 210 is or includes an electrode. As shown in FIG. 2D, the therapy pad 200 may include electrical stimulation modules 210*a* and 210*b*. Each electrical stimulation module 210 may include at least one conductor 211 and at least one pad 212. Each conductor 211 (e.g., conductors 211*a* and 211*b*) may be made of and/or include carbon (e.g., a conductive carbon sheet). Each conductor 211 may be coupled to (e.g., directly attached to) a corresponding pad 212. The electrical stimulation module 210 may conduct an electrical signal (e.g., current and/or voltage) through the corresponding conductor 211 and pad 212 to provide electrical stimulation to a body region of a user. In some embodiments, each conductor 211 may be positioned above the corresponding pad 212, such that each conductor 211 is coupled to (e.g., directly coupled to) each corresponding pad 212. Each conductor 211 may be coupled to the control module 104 or pad control module 204, such that the control module 104 or pad control module 204 can provide an electrical signal to the conductor 211 to administer electrical stimulation. In some embodiments, each conductor 211 may be coupled to the control module 104 or the pad control module 204 by a conductive component (e.g., a wire, a pin, etc.). In such embodiments, the size of the conductor 211 may be reduced and/or otherwise modified, such that the conductor 211 may conduct an electrical signal over a reduced footprint to the corresponding pad 212 as described herein.

In some embodiments, the therapy pad 200 may include an adhesive layer 216. The adhesive layer 216 may be made of plastic. In an example, the adhesive layer 216 may be made of polyethylene terephthalate (PET). In some embodiments, the adhesive layer 216 may include an adhesive on each side (e.g., such that the adhesive layer 216 is a double-sided adhesive layer). A first side of the adhesive layer 216 may include a silicone-based adhesive. The first side may removably adhere to a body region (e.g., skin surface) of a user. In some cases, the first side of the adhesive layer 216 may enable one or more applications of the therapy pad 200 (related therapy device 300 as described below) to a body region of a user. For example, the adhesive layer 216 may enable application of the therapy pad to a body region of a user for about 10 to about 40 therapy sessions. A second side of the adhesive layer 216 may include an acrylic-based adhesive. The second side may adhere to the heat spreader 209. In some embodiments, the adhesive layer 216 may be a double-sided silicone adhesive sheet having a thickness of approximately 0.1-0.3 mm (e.g., 0.2 mm) (e.g., a ScarAway Silicone Scar Sheet or a 3M 2477P sheet). An adhesive (or adhesives) of the adhesive layer 216 may be thermally conductive, such that the heat spreader 209 may propagate heat generated by the resistive component 207 through the adhesive layer 216. In some embodiments, the adhesive layer 216 may be positioned below the heat spreader 209. The adhesive layer 216 may be positioned in a horizontal plane with each pad 212. In use, the adhesive layer 216 may adhere to a body region of a user as described herein.

Referring to FIG. 2E, an exploded view of an exemplary heat generation module 206 for the therapy pad 200 is presented, according to some embodiments. As shown in FIG. 2E, the heat generation module 206 may include a resistive component 207*a*, a backing layer 208*b*, and a heat spreader 209. The backing layer 208*b* may include one or more channels 218. The one or more channels 218 may increase the flexibility of the backing layer 208*b* and may improve application of the therapy pad 200 to a body region of a user as described further below. In some cases, the channels 218 may be die cut during manufacturing of the backing layer 208*b*. The heat generation module 206 may include a temperature sensor 205 as described herein with respect to FIG. 2D.

While the therapy pad 200 shown and described with respect to FIGS. 2A-2E may have a rectangular shape, the therapy pad 200 may be configured to have any suitable shape and/or dimensions based on the application of the therapy pad 200 to a body region of a user. In some cases, the therapy pad 200 may be embodied in a plurality of shapes and/or dimensions to correspond to different body regions of a user. For example, the therapy pad 200 may be additionally or alternatively embodied in an "x" shape for application to a neck region of a user.

Embodiments of a Therapy Device

Various embodiments of the therapy device 300 may include one or more of the vibration module 106, the heat generation module 206, and/or the electrical stimulation module 210. In an embodiment, the therapy device 300 includes a heat generation module 206, but no vibration module 106 and no electrical stimulation module(s) 210. Such an embodiment of the therapy device 300 may be capable of providing heating therapy via the heat generation module 206, but incapable of providing vibration therapy and electrical stimulation therapy as described herein.

In another embodiment, the therapy device 300 includes a heat generation module 106 and a vibration module 206, but no electrical stimulation module 210. Such an embodiment of the therapy device 300 may be capable of providing heating therapy via the heat generation module 206 and vibration therapy via the vibration module 106, but incapable of providing electrical stimulation therapy as described herein.

In another embodiment, the therapy device 300 includes a heat generation module 106 and an electrical stimulation module 210, but no vibration module 206. Such an embodiment of the therapy device 300 may be capable of providing heating therapy via the heat generation module and electrical stimulation therapy via the electrical stimulation module, but incapable of providing vibration therapy as described herein.

In another embodiment, as described herein, the therapy device 300 includes a heat generation module 106, a vibration module 206, and one or more electrical stimulation modules 210. Such an embodiment of the therapy device 300 may be capable of providing heating therapy, vibration therapy, and electrical stimulation therapy.

In some embodiments, as described herein, the housing 102 of the control unit 100 may be shaped as a square prism or a rectangular prism. Other form factors for the housing 102 of the control unit 100 are possible. As an example, the housing 102 may have a cylindrical form factor with a diameter between 50 mm to 100 mm. In some embodiments, as described herein, the therapy pad 200 may be shaped as a square. As an example, the therapy pad 200 may be shaped as a 3 inch by 3 inch square. Other form factors for the therapy pad 200 are possible. As an example, the therapy pad may be shaped as a 3 inch by 6 inch rectangle or as an 8 inch by 10 inch rectangle. Additionally or alternatively, the therapy pad 200 may shaped as a circle or any other suitable shape (e.g., an "x" shape for application to a neck area). In some embodiments, corners of the therapy pad 200 may be rounded.

Functions of a Therapy Device

Figure 3A:
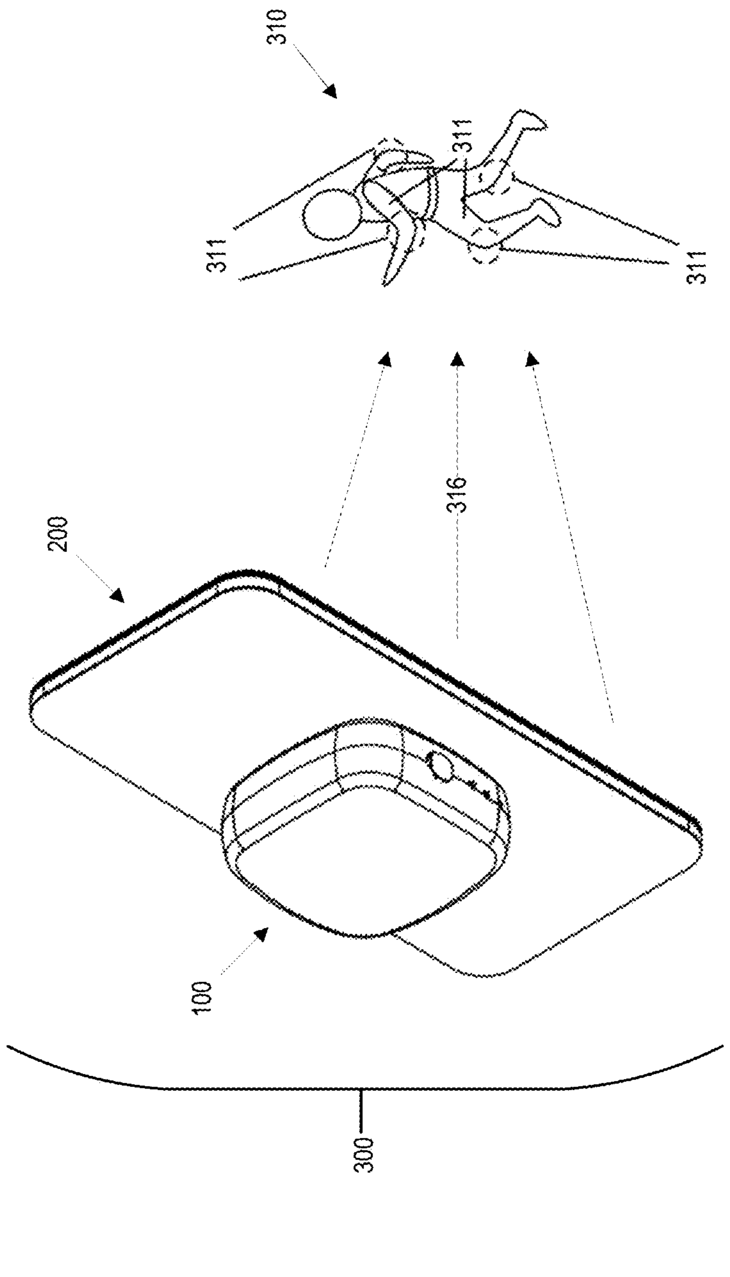
FIG. 3A illustrates an exemplary therapy device, according to some embodiments.
Figure 3B:
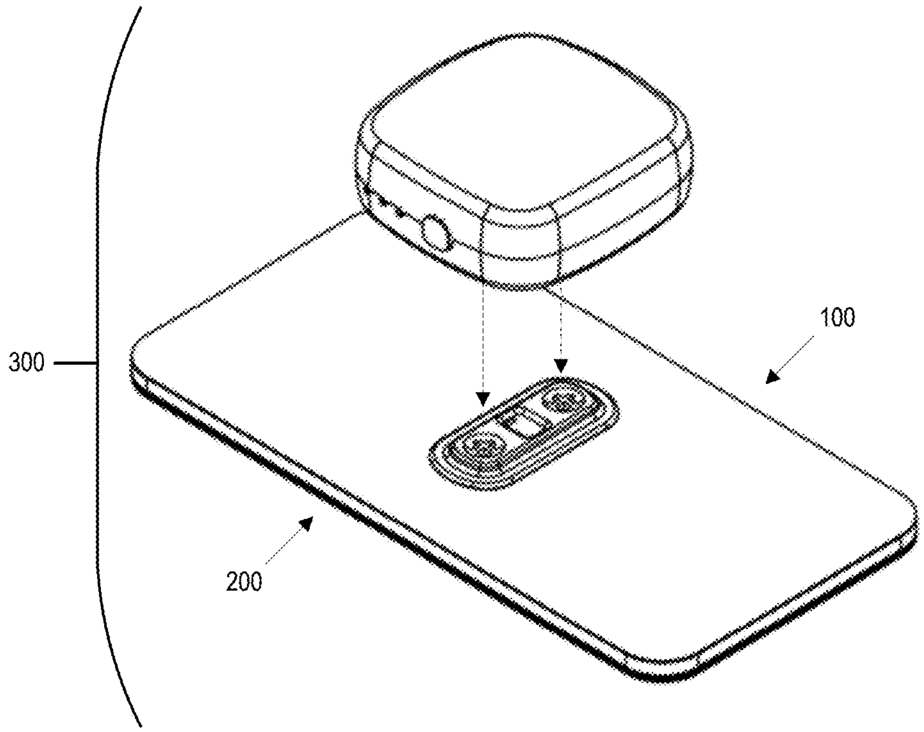
FIG. 3B illustrates another view of the exemplary therapy device, according to some embodiments.

Referring to FIGS. 3A and 3B, a therapy device 300 comprising the control unit 100 and the therapy pad 200 is presented, according to some embodiments. The therapy device 300 can function to provide temperature regulated heating therapy, vibration therapy, and/or electrical stimulation therapy (e.g., TENS therapy) to a body region 311 of a user 310, and in specific examples can provide a combination of heating therapy, vibration therapy, and electrical stimulation therapy to a body region 311 using the same device. The therapy device 300 can be adhered to a body region 311 by the adhesive layer 216 of the therapy pad 200. The adhesive layer 216 may be adhered to a body region 311 (e.g., skin area) such that the adhesive layer 216 and each pad 212 of an electrical stimulation module 210 may be in contact with and/or otherwise adjacent to the body region 311. The therapy device 300 may provide heating therapy via the heat generation module 206 as described herein. The therapy device 300 may provide vibration therapy via the vibration module 106 as described herein. The therapy device 300 may provide electrical stimulation therapy via the one or more electrical stimulation modules 210.

In some embodiments, the therapy device 300 can function to provide heating therapy, vibration therapy, and/or electrical stimulation therapy based on received control instructions (e.g., from a computing device, a mobile application-based controller, a mobile computing platform, a client application execution thereon, etc.). The therapy device 300 may function to monitor and/or track parameters of therapy provision (e.g., administration), such as the temperature of the heating therapy being provided (e.g., administered), the frequency and/or amplitude of the vibrations of the vibration therapy being provided, the frequency, voltage, current, and/or power of the electrical signals of the electrical stimulation therapy being provided, the power and/or energy usage of the therapy device 300 during therapy, and/or any other suitable parameters. In some embodiments, the therapy device 300 may function to track user data such as frequency of use (e.g., daily, hourly, monthly, etc.), duration of use (e.g., total duration in minutes, duration on a per-operating-mode basis, duration on a per-contiguous-use basis, etc.) and therapy selection (e.g., heat therapy, vibration therapy, electrical stimulation therapy), and provide tracked user data to an entity (e.g., the user 310, a physical therapist associated with the user 310, etc.). Such data may be used, for example, to guide automated modes of administering therapy to the user 310.

In some embodiments, the therapy device 300 may store received control instructions corresponding to heating therapy, vibration therapy, and/or electrical stimulation therapy. As an example, the therapy device 300 may store the most recently received control instructions corresponding to heating therapy, vibration therapy, and/or electrical stimulation therapy. In some cases, the therapy device 300 may store and maintain the control instructions from previous uses of the therapy device 300. As an example, to prevent a user from being required to reconfigure control instructions for a present therapy session, the therapy device 300 may maintain control instructions between uses of the therapy device 300. As another example, the therapy device 300 may maintain control instructions (e.g., configured setpoints and/or parameters) for heating therapy, vibration therapy, and/or electrical stimulation therapy between power cycles (e.g., powering on and off).

Referring to FIG. 3A, the therapy device 300 can be positioned at one or more musculoskeletal body regions 311 of the user 310 (e.g., a knee region, a lower back region, an elbow region, etc.). In some embodiments, the therapy device 300 can additionally or alternatively include multiple instances of the therapy device 300, but in the same or different configurations, that can be positioned at disparate regions of the user (e.g., a knee region, a calf region, a lower back region, any other suitable musculoskeletal region, any other suitable body region, etc.). Additionally or alternatively, the therapy device 300 can be placed on a torso region of a user, while positioning another therapy device 300 proximal to another musculoskeletal region (e.g., a lower back region). A direction 316 may be the direction at which the therapy device 300 is positioned on a user 310 via the adhesive layer.

In some embodiments, for a therapy device 300, the control unit 100 and the therapy pad 200 may be coupled via the coupling mechanisms 116 and 218 as described herein. The coupling mechanisms 116 and 218 may be physically coupled (and decoupled) via one or more magnets (e.g., the magnets 116*a* and 116*b*). In an example, as shown in FIG. 3A, the coupling mechanism 116 of the control unit 100 may couple to the coupling mechanism 218 of the therapy pad 200 via magnetism. Any suitable physical coupling mechanism may be used by the coupling mechanisms 116 and 218 to couple the control unit 100 and the therapy pad 200. In some embodiments, when the coupling mechanisms 116 and 218 are coupled, the pad interface 112 and I/O channel 214 may be communicatively and/or electrically coupled. In some embodiments, the pad interface 112 and I/O channel 214 may be communicatively and/or electrically coupled via one or more pins (e.g., pogo pins), such that the control module 104 of the control unit 102 and may be communicatively and/or electrically coupled to one or more components of the therapy pad (e.g., the pad control module 204, heat generation module 206, temperature sensor 205, and/or electrical stimulation module(s) 210). Any suitable wired connection and/or wireless communication protocol described herein may be used to communicatively and/or electrically couple the pad interface 112 and I/O channel 214.

In some embodiments, one or more pins of the coupled pad interface 112 and I/O channel 214 may be dedicated to configured communication types. In an example, there may be 8 pins (e.g., pogo pins) coupling the pad interface 112 and I/O channel 214, where 2 pogo pins are dedicated to communications between the control module 104 and pad control module 204, 2 pogo pins are dedicated to coupling the control module 104 to the temperature sensor 205, 2 pogo pins are dedicated to coupling the control module 104 to the heat generation module 206 (e.g., to the resistive component 207), and 2 pogo pins dedicated to coupling the control module 104 to the electrical stimulation module(s) 210 (e.g., to the conductor(s) 211). In an example, if the therapy pad 200 does not include the electrical stimulation module(s) 210, there may be 6 pins coupling the pad interface 112 and the I/O channel 214. In an example, if the therapy pad 200 does not include the heat generation module 206, there may be 5 pins coupling the pad interface 112 and the I/O channel 214. In an example, if the control unit 100 does not include the vibration module 106, there may be 8 pins coupling the pad interface 112 and the I/O channel 214 as described herein. Any suitable number of pins may be used to communicatively couple the control unit 100 and the therapy pad 200 as described herein. In some embodiments, the control module 104 and the pad control module 204 may communicate over the coupled I/O channels 112 and 114 via encrypted and/or serialized communications. The control unit 100 may provide power to the therapy pad 200 via the coupled pad interface 112 and I/O channel 214 as described herein. In some embodiments, based on coupling the control unit 100 and therapy pad 200, the control unit 100 may authenticate the therapy pad 200 according to an authentication method as described herein.

In some embodiments, the therapy pad 200 of the therapy device 300 may be decoupled from the control unit 100, such that the therapy pad 200 may be replaced. The therapy pad 200 may be consumable, such that one or more elements of the therapy pad 200 may degrade as the therapy pad is used as a part of the therapy device 300. As such, the therapy device 300 may track usage information for the therapy pad 200 (e.g., may track the number of times the therapy pad 200 has been used to administer therapy). The usage information may include a unique identifier corresponding to a therapy pad 200, where each therapy pad 200 includes a unique identifier. In some embodiments, the therapy device 300 may track the duration of each use of the therapy pad 200 and the therapy or therapies administered during use of the therapy pad 200. The therapy device 300 may determine a therapy pad 200 to need replacement based on the usage of the therapy pad 200 exceeding a threshold number of uses. In an example, the threshold number of uses may be 10 uses of the therapy pad 200, wherein each of the 10 uses exceeds a threshold duration. Additionally or alternatively, the therapy device 300 may determine a therapy pad 200 to need replacement based on the usage of the therapy pad 200 exceeding an aggregate threshold duration of time. In an example, the aggregate threshold duration of time may be 5 hours. In some embodiments, the therapy device 300 may track the number of therapy pads 200 that have been used with the therapy device. In an example, the therapy device 300 may track that 12 different therapy pads 200 have been used by the control unit 100 as a part of usage information.

In some embodiments, the usage information tracked by the therapy device 300 may be communicated to an external computing device (e.g., the computing device 120). The usage information may be communicated to an external computing device via a client application. The external computing device may store the usage information locally (e.g., within a client application) and/or store the usage information in a cloud computing storage medium (e.g., accessible via a client application). The usage information may displayed at the client application. Based on the identifier associated with a therapy pad 200, usage information may be communicated to the therapy device 300 (e.g., via an external computing device) such that the therapy device may determine the usage information corresponding to the therapy pad 200. In some embodiments, the usage information tracked by the therapy device 300 may be stored on a memory of a therapy pad 200. A therapy device 300 may determine usage information for a particular therapy pad 200 based on the usage information stored in the memory of the therapy pad 200.

Referring to FIGS. 1A, 2A, and 3A-3B, in some embodiments, the therapy device 300 can include a control module 104. The control module 104 can determine control instructions (e.g., received at an input of the therapy device 300 or via a computing device 120) and control the vibration module 106 according to the determined control instructions. The control module may also control the heat generation module 206 and the one or more electrical stimulation modules 210. In some embodiments, the control module 104 can receive control instructions and/or generate control instructions (e.g., at a mobile computing device platform or application, an integrated user interface, etc.). For example, the control module 104 may receive control instructions from a client application operating at a computing device 120 as to be described herein. The control module 104 can include a processor, memory, and/or a communications module as described herein. In some embodiments, the control module 104 can be communicatively coupled to a computing device 120 of the user (e.g., via a Wi-Fi, Bluetooth, Bluetooth low-energy/BLE, or any other suitable wireless communication protocol; via a wired connection; etc.). The control module 104 can be at least partially controlled through a mobile application platform of a computing device 120. In some embodiments, the control module 104 can be communicatively coupled to another computing device, such as a tablet, laptop computing device, desktop computing device, etc., via a wireless connection as described herein. Additionally or alternatively, the control module 104 may be communicatively coupled to a computing device 120 (or other computing device) via the I/O interface 110. In an example, the control module 104 of the therapy device 300 may be coupled to the computing device 120 via a USB-C connection.

In some embodiments, the control module 104 of the therapy device 300 may receive control instructions from the computing device 120 (or another computing device). A computing device 120 (or other computing device) may control any suitable number of therapy devices 300. The computing device 120 may control the number of therapy devices 300 independently, such that each therapy device 300 may be configured for independent therapy(ies). Additionally or alternatively, the computing device 120 may control the number of therapy devices in synchronization, such that each therapy device 300 is configured for the same therapy(ies). For example, a computing device 120 may independently control five control modules 104 (and corresponding therapy devices 300) via a Bluetooth connection, such that the computing device 120 can control heating therapy, vibration therapy, and/or electrical stimulation therapy for each therapy device 300 independently. In some embodiments, a computing device 120 may coordinate the control of two or more therapy devices 300, such that therapy devices 300 cooperate to administer related or mutually beneficial therapies as part of a coordinated therapeutic program.

In some embodiments, when a control unit 100 and a therapy pad 200 are communicatively coupled, the control module 104 may authenticate the therapy pad 200. The control module 104 may authenticate the therapy pad 200 based on communicating encrypted information with the pad control module 204. The control module 104 may perform an authentication method to authenticate the therapy pad 200 as described herein.

In some embodiments, the control module 104 may apply a control voltage to the vibration module 106. The control module 104 may apply a control voltage based on received control instructions from a computing device 120. Application of the control voltage to the vibration module 106 may induce vibration of the vibration module 106 as described herein, providing vibration therapy at a body region 311. As described herein, the control module 104 may be electrically and/or communicatively coupled to the vibration module 106.

In some embodiments, the control module 104 may apply a control voltage to the heat generation module 206 such that a desired temperature is generated by the resistive component 207, thereby heating a body region 311. The control module 104 may duty-cycle the control voltage applied to the heat generation module 206 based on a difference between a temperature measured at the heat generation module 206 and a target temperature (e.g., temperature setpoint) of the heat generation module 206. The control module 104 can be communicatively and/or electrically coupled to the heat generation module 206 of the therapy pad 200 via the pad control module 204. In some embodiments, the control module 104 may be coupled (e.g., directly coupled) to the heat generation module 206 via the coupled pad interface 112 and I/O channel 214.

In some embodiments, the control module 104 may be coupled to one or more indicators as described herein. The one or more indicators may be included in the housing 102. The one or more indicators may each include an LED. In some embodiments, each LED may be illuminated in one or more colors. The control module 104 may illuminate the one or LEDS based on the one or more functions of the therapy device 300. The control module 104 may be configured to illuminate or deactivate the one or more LEDs based on usage (e.g., battery life) of the therapy device 300, authentication of the therapy pad 200, or identification of the therapy device. In an example, an indicator may illuminate as a red color based on the battery life of the therapy device 300 dropping below a threshold power value. In an example, if more than one therapy device 300 is connected to a computing device (and client application), control modules 104 may activate indicators of each therapy device 300 in one or more different sequences or colors to differentiate each therapy device 300, such that each therapy device 300 may be identified. Activation of the one or more indicators may correspond to information presented by the client application as described herein. For example, a pair of therapy devices 300 may each have an indicator with an LED, where a color of each illuminated LED may correspond to colors (or other identifiers) presented at a client application that are indicative of each therapy device 300.

In some embodiments, the control module 104 can be coupled to a temperature sensor 205 that functions to monitor the temperature at the heat generation module 206. An output of the temperature sensor 205 (e.g., an analog or digital signal indicative of the temperature of the heat generation module 206) can be provided to the control module 104 via a direct data connection (e.g., a serial bus, a double-ended signal transmission wire pair, etc.) of the pad interface 112 and I/O channel 214, or can be otherwise suitably coupled to the control module 104 (e.g., via the pad control module 204). The temperature sensor 205 may be positioned adjacent or proximal to one or more of: the resistive component 207, the backing layer 208, and the heat spreader 209. In some embodiments, a single temperature sensor 205 may be positioned at the heat generation module 206. In some embodiments, the heat generation module 206 can additionally or alternatively include any suitable number of temperature sensors coupled directly and/or indirectly to the control module 104. The temperature sensor 205 can include any suitable type of temperature sensor, such as contact sensors (e.g., thermocouples, thermistors, digital thermometers, analog thermometers, etc.) or non-contact sensors (e.g., infrared thermometers, radiative temperature sensors, scattered emission thermometers, etc.).

In some embodiments, the control module 104 may be coupled to one or more accelerometers. One or more accelerometers may be distributed within the therapy device 300, including the control unit 100 and/or the therapy pad 200. In some embodiments, the one or more accelerometers may be included in the therapy pad 200 adjacent to the pads 212 (e.g., embedded in the adhesive layer 216 adjacent to the pads 212) or embedded within the pads 212. An accelerometer of the therapy device 300 may measure acceleration of the therapy device 300 and/or its elements (e.g., the control unit 100 or the therapy pad 200). In an example, an accelerometer coupled to the control module 104 and positioned within the control unit 100 may record acceleration data for the control unit 100. Such acceleration data may be used to track movements and/or motion of a user 310 at a particular body region 311. In some embodiments, an accelerometer may be positioned within the therapy device 300 to measure acceleration associated with muscle twitching from a body region 311, where the muscle twitching may result from electrical stimulation therapy. In some embodiments, acceleration data from one or more accelerometers coupled to the control module 104 may be used to model the movement(s) of a user 310 for further analysis, such as by a therapy professional. As described herein, one or more therapy devices 300 may be coupled to a computing device 120 and/or another computing device (e.g., a tablet computing device operated by a therapy professional). Accordingly, acceleration data recorded by accelerometers from more than one therapy device 300 may be captured by the therapy devices and sent (e.g., via Bluetooth or any other suitable wired or wireless connection) to another computing device (e.g., the computing device 120) for further analysis.

In some embodiments, the control module 104 may be coupled to one or more pressure sensors. One or more pressure sensors may be distributed within the therapy device 300, including the control unit 100 and/or the therapy pad 200. In an example, a pressure sensor may be embedded within an pad 212. A pressure sensor of the therapy device 300 may measure pressure at a body region 311 to which the therapy device 300 is adhered. In an example, a pressure sensor coupled to the control module 104 and positioned within the therapy pad 200 may record pressure data for the control unit 100. Such pressure data may be used to track and/or identify pressure changes at a particular body region 311. In some embodiments, a pressure sensor may be positioned within the therapy device 300 to measure pressure differences associated with muscle twitching from a body region 311, where the muscle twitching may result from electrical stimulation therapy. In some embodiments, pressure data from one or more pressure sensors coupled to the control module 104 may be used to model the movement (s) of a user 310 for further analysis, such as by a therapy professional. As described herein, one or more therapy devices 300 may be coupled to a computing device 120 and/or another computing device (e.g., a tablet computing device operated by a therapy professional). Accordingly, pressure data recorded by pressure sensors from more than one therapy device 300 may be captured by the therapy devices and sent (e.g., via Bluetooth or any other suitable wired or wireless connection) to another computing device (e.g., the computing device 120) for further analysis.

In some embodiments, the control module 104 may be coupled to an optical sensor. The optical sensor may be positioned within the therapy device 300 such that the optical sensor may measure the temperature at a body region of a user. The optical sensor may be an infrared temperature sensor. In an example, the therapy device 300 may include a cavity such that the optical sensor may emit a signal that may reach the body region of a user, such that the optical sensor can aggregate temperature information from a surface of the body region. The temperature information measured by the optical sensor may be used to provide heating therapy as described herein.

In some embodiments, the control module 104 may apply a control voltage and/or current to one or more electrical stimulation modules 210, such that the electrical stimulation module(s) 210 provide electrical stimulation to a body region 311. The control module 104 may apply a configurable control voltage to enable varying pulse frequencies, pulse widths, and/or intensity (e.g., power) levels for the electrical stimulation provided by the electrical stimulation module(s) 210. The control module 104 can be communicatively and/or electrically coupled to the electrical stimulation module(s) 210 of the therapy pad 200 via the pad control module 204. In some embodiments, the control module 104 may be coupled (e.g., directly coupled) to the electrical stimulation module(s) 210 via the coupled pad interface 112 and I/O channel 214.

In some embodiments, the electrical stimulation module (s) 210 may provide transcutaneous electrical nerve stimulation (TENS) to stimulate nerves of a user 310. The electric stimulation module(s) 210 may provide electrical muscle therapy (EMS) to stimulate (e.g., cause contraction) muscle cells of a user 310. In some embodiments, the electrical stimulation module(s) 210 may provide EMS using neuromuscular stimulation. The electrical stimulation module(s) may provide neuromodulation therapy to a user 310. Any suitable electrical stimulation therapy may be provided by the electrical stimulation module(s) 210 via one or more electrical signals. The one or more electrical signals may include electrical waveforms and/or pulses.

Referring to FIGS. 1A and 3, in some embodiments, the therapy device 300 can include a vibration module 106. The vibration module 106 may enable the therapy device 300 to provide vibration therapy to a body region 311. The vibration module 106 may include a vibration motor. In some embodiments, the vibration motor is a coin cell vibration motor. In some embodiments, the vibration motor may include a motor rotationally coupled to a shaft having a first end and a second end. The motor may be rotationally coupled to the first end of the shaft such that the motor may rotate the shaft during operation of the motor. The second end of the shaft may be coupled to an eccentric mass, where the eccentric mass may rotate about an axis of the shaft during operation of the motor. During operation of the motor, the shaft and eccentric mass may rotate such that vibration is induced by the vibration module 106. The vibration module 106 may receive a control voltage (e.g., control signal) from the control module 104 such that the motor and coupled eccentric mass may rotate (and cause vibration of the vibration module 106) at a configured frequency. In an example, the motor may operate at 2-4 V (e.g., 3 V). In an example, the motor may be a permanent magnet, direct current (DC) motor operating at 5300 rotations per minute (RPM). In an example, the motor may operate at 11,500 RPM or 7,000 RPM. In some embodiments, the rotation of the motor may be configured at the control unit 100 as described herein with respect to control instructions. The motor may operate between approximately 5000 RPM and 12,000 RPM.

Referring to FIGS. 1A and 3A-3B, in some embodiments, the therapy device 300 can include a power supply module 108, which can provide electrical power to the control module 104, such that the control module 104 can provide power to the vibration module 106 and the therapy pad 200 (e.g., the pad control module 204, the heat generation module 206, the electrical stimulation module(s) 210, etc.). The power supply module 108 can store energy to provide portable functionality (e.g., portability) to the system. The power supply module 108 can include an energy storage device (e.g., a battery), power regulation circuitry, a charging interface, and/or any other suitable components for power supply and storage. In some embodiments, the power supply module may supply 2.5 V-5.0 V (e.g., 3.7 V) to the control module 104 (and other elements of the therapy device 300). In some embodiments, a charging interface of the power supply module 108 may be coupled to the I/O interface 110. In an example, the charging interface may support USB-C, such that the power supply module 108 may receive power via a USB-C connector coupled to the I/O interface 110. The power supply module 108 may be coupled to the control module 104 via direct electrical connection, conductive traces, wires, an electrical cable, etc. In some embodiments, the power supply module 108 can be coupled (e.g., via the charging interface) to a source of grid power (e.g., alternating current, regulated direct-current, wall power, etc.). The power supply module 108 can be otherwise suitably coupled to other components of the control unit 100 or therapy pad 200 in any suitable manner.

The therapy device 300 may provide heating therapy at a temperature up to at least 110° F. based on low voltage signal (e.g., 3.7 V) supplied by the power supply module 108. Providing heating therapy at a temperature up to at least 110° F. using a low voltage signal may be enabled based on the combination of the resistive component 207, the heat spreader 209, and the adhesive layer 216. The resistive component 207, the heat spreader 209, and the adhesive layer 216 may function within the therapy device 300 to provide efficient heat generation, without loss of thermal energy due to excess insulation and/or poor thermal coupling to a body region 311 of a user 310. The heat spreader 209 may distribute heat generated by the resistive component 207 and the silicone based adhesive may efficiently thermally couple the therapy device 300 to a body region 311.

Referring to FIGS. 1A, 2A, and 3A-3B, in some embodiments, the therapy device 300 can include a pad control module 204 as part of the therapy pad 200. In some embodiments, the pad control module 204 can determine control instructions (e.g., received from the control module 104) and control the heat generation module 206 and/or the electrical stimulation modules 210 according to the determined control instructions. In some embodiments, the pad control module 204 may receive control instructions (e.g., for the heat generation module 206 and/or the electrical stimulation modules 210) from the control module 104. In other embodiments, the control module 104 may directly control the heat generation module 206 and/or the electrical stimulation modules 210, thereby bypassing the pad control module 204. The pad control module 204 can include a processing device (e.g., processor, microcontroller, micro-control unit, etc.), memory (e.g., non-volatile memory), and/or a communications module.

In some embodiments, based on coupling the control unit 100 and the therapy pad 200 such that the pad interface 112 and I/O channel 214 are coupled (e.g., via one or more pogo pins), the control module 104 may authenticate the therapy pad 200 via the pad control module 204. The pad control module 204 may communicate encrypted information to the control module 104 to authenticate the therapy pad 200. The pad control module 204 may perform an authentication method to authenticate the therapy pad 200 as described herein.

In some embodiments, if the pad control module 204 is configured to control elements of the therapy pad 200 (e.g., based on instructions from the control module 104), the pad control module 204 may apply a control voltage to the heat generation module 206 such that a desired temperature is generated by the resistive component 207, thereby heating a body region 311. The pad control module 204 may duty-cycle the control voltage applied to the heat generation module 206 based on a difference between a temperature measured at the heat generation module 206 and a target temperature (e.g., temperature setpoint) of the heat generation module 206. The pad control module 204 can be communicatively and/or electrically coupled to the heat generation module 206. In some embodiments, the pad control module 204 may communicate feedback information from the heat generation module 206 to the control module 104 via the coupled pad interface 112 and I/O channel 214.

In some embodiments, the pad control module 204 can be coupled to the temperature sensor 205 that functions to monitor the temperature at the heat generation module 206 as described herein. An output of the temperature sensor 205 (e.g., an analog or digital signal indicative of the temperature the heat generation module 206) can be provided to the pad control module 104 via a direct data connection (e.g., a serial bus, a double-ended signal transmission wire pair, etc.) of the pad interface 112 and I/O channel 214, or can be otherwise suitably coupled to the control module 104 (e.g., via the pad control module 204) as described herein. In some embodiments, the pad control module 204 may provide the output of the temperature sensor 205 to the control module 104 via the coupled pad interface 112 and I/O channel 214.

In some embodiments, the pad control module 204 can be coupled to one or more accelerometers with the functionality as described herein with respect to the control module 104. The pad control module 204 may communicate recorded accelerometer data for one or more accelerometers located at the therapy pad to the control module 104.

In some embodiments, if the pad control module 204 is configured to control elements of the therapy pad 200 (e.g., based on instructions from the control module 104), the pad control module 204 may apply a control voltage to one or more electrical stimulation modules 210, such that the electrical stimulation module(s) 210 provide electrical stimulation to a body region 311. The pad control module 204 may apply a control voltage at varying a frequency and/or power level to modulate the electrical stimulation provided by the electrical stimulation module(s) 210. The pad control module 204 can be communicatively and/or electrically coupled to the electrical stimulation module(s) 210. In some embodiments, the pad control module 204 may communicate feedback information from the electrical stimulation module(s) 210 to the control module 104 via the coupled pad interface 112 and I/O channel 214.

Referring to FIGS. 1A, 2A, and 3A-3B, in some embodiments, the therapy device 300 can include a heat generation module 206. The heat generation module 206 can function to provide an interfacial surface (e.g., between the therapy device 300 and a body region 311) having a controllable temperature to provide heating therapy. The heat generation module 206 can be coupled to the pad control module 204 and/or to the control module 104. The connection may be a direct and/or an indirect electrical connection. The connection may be configured to supply electrical power and/or send and receive data (e.g., control instructions, feedback information, etc.). The heat generation module 206 may receive a control voltage from the pad control module 204 and/or from the control module 104. In an example, the heat generation module 206 may receive a control voltage from the pad control module 204 based on the pad control module 204 receiving control instructions from the control module 104. Alternatively, in an example, the heat generation module 206 may receive a control voltage from the control module 104 via the coupled pad interface 112 and I/O channel 214. Based on receiving a control voltage, the heat generation module 206 may generate thermal energy to heat a body region 311 as to be described herein.

In some embodiments, as described herein, the heat generation module 206 can include a resistive component 207, a backing layer 208 for the resistive component 207, and a heat spreader 209. The resistive component 207 of the heat generation module 206 can provide a thermomechanical interface through which heat is exchanged with a body region 311. A received control voltage at the heat generation module 206 may be applied to the resistive component 207. In an example, the control voltage applied to the resistive component 207 may be 2.5 V-5.0 V (e.g., 3.7 V). Based on the control voltage being applied to the resistive component 207, a current may conduct through the resistive component 207, such that heat is generated as a byproduct of resistive component 207 impeding the flow of the current. Based on the applied control voltage, the resistive component 207 may generate a high temperature (e.g., 100-120° F.) to provide heating therapy. In some embodiments, the resistive component 207 may include one or more configurations. In an example, as shown in FIG. 2D, a resistive component 207*a* may be of a substantially rectangular configuration. In another example, as shown in FIG. 2E, a resistive component 207*b* may be of a maze-like or "mitochondria-like" configuration. In other embodiments, the resistive component 207 may be of a circular configuration. In some embodiments, the ratio of the length of the resistive component 207 to the perimeter of the backing layer 208 may be less than 1.0 (e.g., between 0.6 and 1.0). The configuration (e.g., shape, size, dimensions, etc.) of the resistive component 207 may be based on a configuration and/or an application of the therapy pad 200.

In some embodiments, the heat generation module 206 may include the backing layer 208 as a medium on which the resistive component 207 is coupled. The backing layer 208 may be made of polyamide as described herein. For example, the resistive component 207 may be printed on the backing layer 208. In other embodiments, the heat generation module 206 may not include the backing layer 208, such that the resistive component 207 is positioned adjacent and/or proximal to the heat spreader 209. In some embodiments, the heat generation module 206 can include a heat spreader 209. The heat spreader 209 may distribute heat generated by the resistive component 207 over the area encompassed by the heat spreader 209. The heat spreader 209 may distribute heat from the resistive component 207 such that the temperature at the resistive component 207 and the temperature at the heat spreader 209 are substantially similar. In an example, the temperature difference between the resistive component 207 and the heat spreader 209 may vary between 5° F. and 15° F. during heating therapy. In an example, as shown in FIG. 2D, the heat spreader 209 may distribute heat generated by the resistive component 207 over a substantially rectangular area covered by the heat spreader 209. Some non-limiting examples of techniques for controlling the heat generation module 206 to generate a specified temperature at the bottom surface of the therapy pad 200 (or at the surface of the region of the user's body to which the therapy pad is applied) are described below.

Referring to FIGS. 1A, 2A, and 3A-3B, in some embodiments, the therapy device 300 can include one or more electrical stimulation modules 210. Each electrical stimulation module 210 may include a conductor 211 and a pad 212 as described herein. Each electrical stimulation module 210 may receive an applied control voltage from the control module 104 (or the pad control module 204), such that each electrical stimulation module 210 provides electrical stimulation to a body region 311 via the pads 212. The received control voltage may be of a varying a frequency and/or power level, such that the parameters of the electrical stimulation therapy provided by the electrical stimulation module may be configured based on received control instructions (e.g., at the control module 104). The electrical stimulation therapy provided by each electrical stimulation module 210 may include periodic electrical impulses applied to a body region 311 of the user 320 via each conductor 211 and each pad 212. Each conductor 211 may transport and/or otherwise conduct a received control voltage (and associated current) to a corresponding pad 212. In an example, as shown in FIG. 2D for the electrical stimulation module 210*a*, the conductor 211*a* may conduct a control voltage and current to the pad 212*a*. Each pad 212 may provide an interfacial surface between the therapy device 300 and a body region 311, such that the therapy device 300 may provide electrical stimulation therapy. Each pad 212 may include, be made of, or be coated by a hydrogel that conducts one or more electrical impulses to a body region 311 to provide electrical stimulation therapy. Each pad 212 may be secured in a position adjacent to a body region 311 by the adhesive layer 216. In some embodiments, each pad 212 may adhere to a skin area of a user 310, such that the skin area can receive electrical stimulation therapy from each pad 212.

Authentication Method for a Therapy Pad

In some embodiments, when the control unit 100 is coupled to the therapy pad 200, the control unit 100 may authenticate the therapy pad 200. The control unit 100 may authenticate the therapy pad 200 to prevent the use of unauthorized therapy devices with the control unit 100. For example, a third party may attempt to manufacture an unauthorized version of the therapy pad 200 for use with the control unit 100. By authenticating a therapy pad 200 via the control unit 100, the control unit 100 can operate to provide therapy to a user in combination with only authorized and/or otherwise authenticated therapy pads 200. In some embodiments, in addition to authenticating the therapy pad 200, the control unit 100 may determine the usage of the therapy pad 200. For example, the control unit 100 may determine the duration of use of the therapy pad 200 or the number of uses of the therapy pad 200. Based on determining that the therapy pad 200 is not authentic or that a usage threshold (e.g., duration, number of uses, etc.) has been exceeded for the therapy pad 200, the control unit 100 may be prevent and/or otherwise deactivate the control unit 100 from enabling the therapy pad 200 to provide vibration, heating, and/or electrical stimulation therapy as described herein. In some embodiments, based on determining a usage threshold has been exceeded for the therapy pad 200, the control unit 100 may send an indication to a computing device (e.g., the computing device 120) that the usage threshold has been exceeded. For example, based on reaching ten uses of the therapy pad 200, the control unit 100 may send a message for display at a client application of the computing device 120, wherein the message indicates the therapy pad needs replacement.

In some embodiments, the control unit 100 may authenticate the therapy pad 200 based on an encrypted handshaking protocol. In some embodiments, data communicated between the control unit 100 and the therapy pad 200 pursuant to the handshaking protocol may be encrypted using an Advanced Encryption Standard (AES) algorithm. In other embodiments, one or more alternative encryption algorithms may be used. During manufacturing of the control unit 100 and/or the therapy pad 200, a private key (e.g., a 128-bit private key) may be stored in a non-volatile memory of the control unit 100 (e.g., at the control module 104) and in a non-volatile memory of the therapy pad 200 (e.g., at the pad control module 204). In some embodiments, the private key may be a randomly (e.g., pseudo-randomly) generated 128-bit encryption/decryption key, such that the private key may be used for encryption and decryption.

Figure 4A:
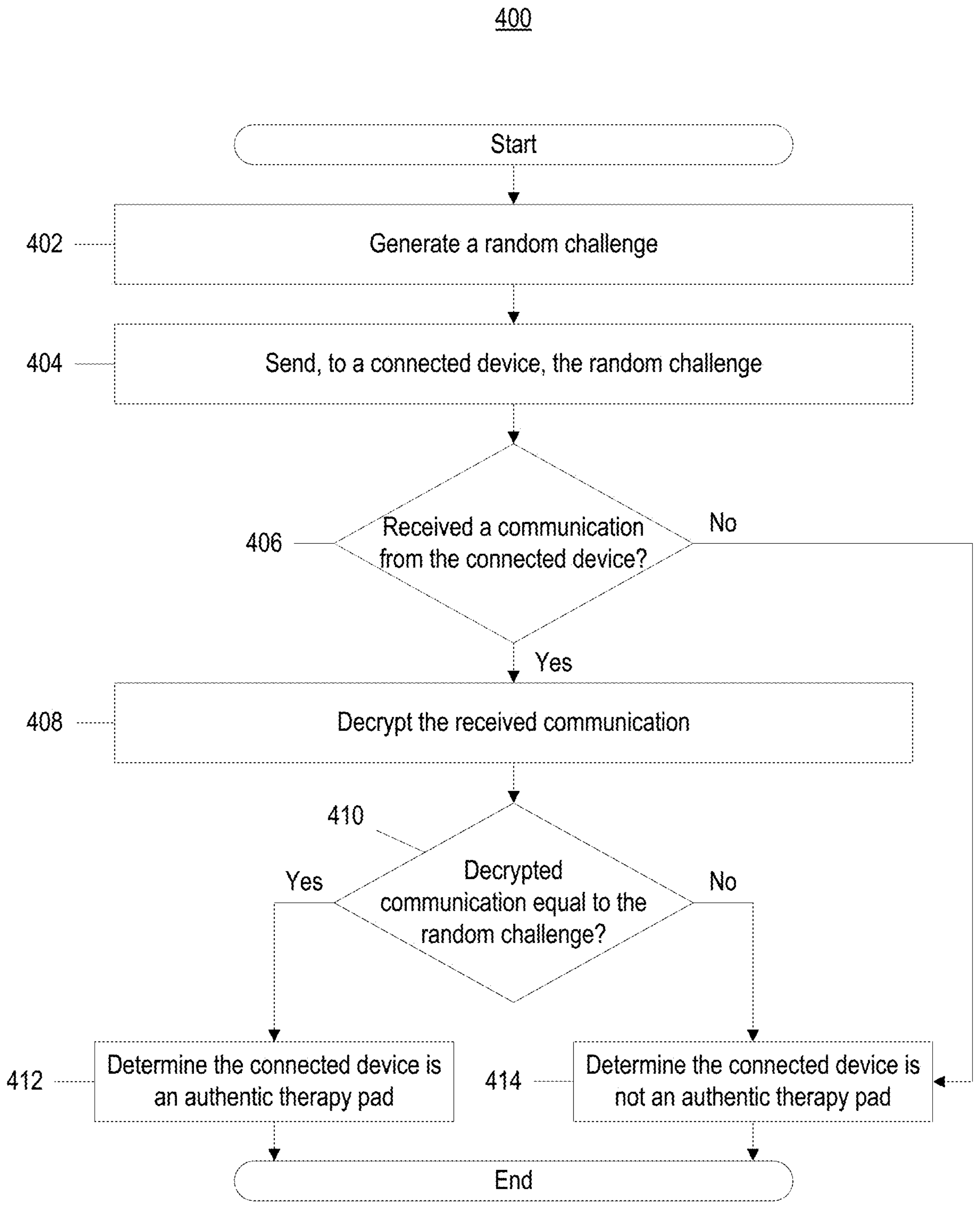
FIG. 4A illustrates a flowchart of an exemplary method for authentication of an exemplary therapy pad by an exemplary control unit, in accordance with some embodiments.

Referring to FIG. 4A, a flowchart of a method 400 for authenticating a connected device (e.g., therapy pad 200) by a control unit (e.g., control unit 100) is presented, in accordance with some embodiments. In some embodiments, at step 402, the control unit may generate a random (e.g., pseudorandom) challenge (e.g., a 128-bit value). The control unit may generate the random challenge based on determining the control unit is connected to a computing device (e.g., at pad interface 112 via coupling mechanism 116). In an example, the computing device may be a therapy pad (e.g., therapy pad 200). In another example, the computing device may be a computing device manufactured by a third party entity to imitate the therapeutic functionality of a therapy pad. A control module (e.g., control module 104) of the control unit may generate the random challenge. In some embodiments, the random challenge may be a 128-bit value.

At step 404, the control unit may send the random challenge to the connected device. The control module may send the random challenge via a pad interface (e.g., pad interface 112). If the connected device is the therapy pad, the control module may send the random challenge to a pad control module (e.g., pad control module 204) of the therapy pad via the coupled pad interface and an I/O channel (e.g., I/O channel 214) as described herein. At step 406, the control unit may monitor for a communication from the connected device and determine whether the control unit has received a communication. In some embodiments, the control unit may monitor for the communication for no more than a threshold amount of time. In an example, the threshold amount of time may be a duration after which the control unit sent the random challenge to the connected device. At step 408, the control unit may decrypt a received communication from the connected device. The control unit may decrypt the received communication if the control module received a communication from the connected device via the pad interface. The control module may decrypt the received communication using the private key as described herein according to AES decryption techniques. Alternatively, at step 414, the control unit may determine the connected device is not an authentic therapy pad. The control unit may determine the connected device is not an authentic therapy pad if the control unit determines a communication has not been received from the connected device (e.g., within a threshold duration of time after sending the random challenge).

At step 410, the control unit may compare the decrypted communication to the random challenge (of steps 402 and 404) and determine whether the decrypted communication and the random challenge are equivalent. The control unit may determine the decrypted communication and the random challenge to be equivalent if the received communication was previously encrypted using the private key (e.g., by the therapy pad 200). At step 412, the control unit may determine the connected device to be an authentic therapy pad. The control unit may determine the connected device to be an authentic therapy pad based on determining the decrypted communication to be equivalent to the random challenge. The decrypted communication being equivalent to the random challenge may indicate the connected device to be the therapy pad, as the therapy pad may store the private key and use the private key for encryption and/or decryption as described herein. Alternatively, as described herein at step 414, the control unit may determine the connected device is not an authentic therapy pad. The control unit may determine the connected device is not an authentic therapy pad based on determining the decrypted communication to be different from the random challenge. The decrypted communication being different from the random challenge may indicate the connected device is not an authentic therapy pad, as the connected device would not include the private key to encrypt the random challenge received from the control unit.

Figure 4B:
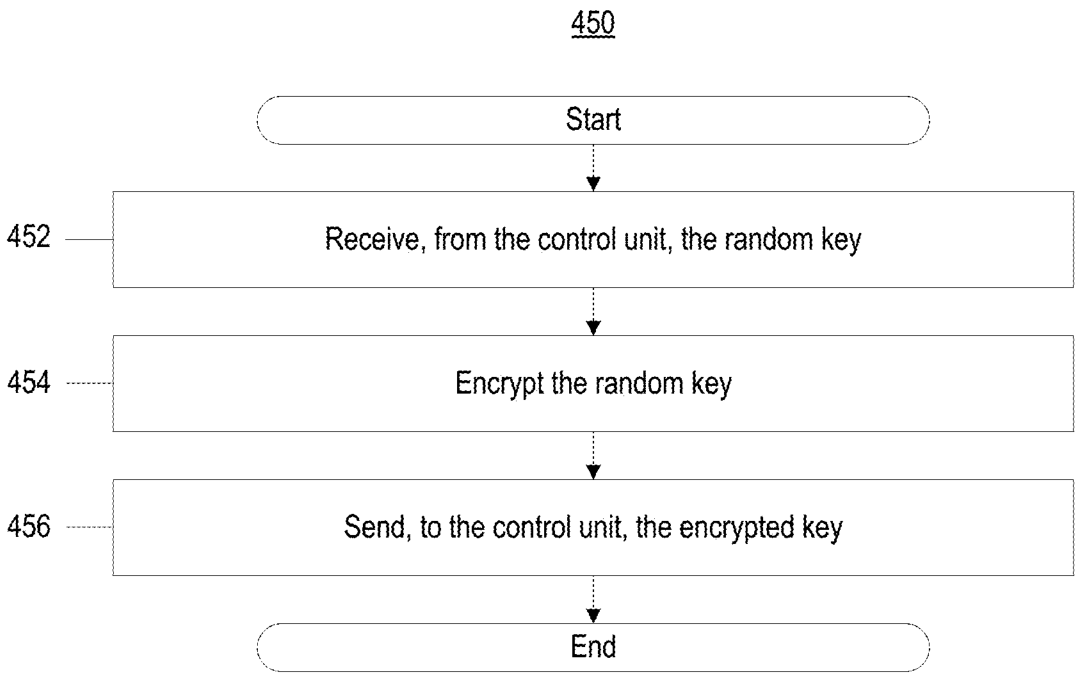
FIG. 4B illustrates a flowchart of an exemplary authentication method of an exemplary therapy pad, in accordance with some embodiments.

Referring to FIG. 4B, a flowchart of a method 450 for authenticating a therapy pad (e.g., therapy pad 200) is presented, in accordance with some embodiments. In some embodiments, at step 452, the therapy pad may receive a random challenge from the control unit. The therapy pad may receive the random challenge from the control unit after coupling to the control unit (e.g., within a configured duration of time). The therapy pad may receive the random challenge from the control unit via the coupled pad interface and I/O channel at the receiver control unit. At step 454, the therapy pad may encrypt the random challenge. The receiver control unit may encrypt the random challenge using the private key as described herein (e.g., according to AES encryption techniques). At step 456, the therapy pad may send the encrypted challenge to the control unit. The receiver control unit may send the encrypted challenge via the coupled pad interface and I/O channel. The encrypted challenge sent by the therapy pad may be decrypted by the control unit, such that the decrypted challenge may be compared to the random challenge sent to the therapy pad to determine whether the therapy pad is authentic.

Control of a Therapy Device

Referring to FIGS. 1A, 2A, and 3A-3B, in some embodiments, the therapy device 300 can receive control instructions to provide vibration, heating, and/or electrical stimulation therapy. Control instructions may be received at one or more input devices of the control unit 100. The one or more input devices may include one or more of: a push-button, a slider, a knob, a touch panel (e.g., a touch sensitive liquid crystal digital (LCD) display)). The input devices and/or the inputs received via the input devices may correspond to one or more operational modes and/or operational levels. In an example, four push buttons of the therapy device 300 may correspond to four different heating levels (e.g., at 102° F., 104° F., 106° F., and 108° F.). In another example, a slider may correspond to an frequency (e.g., intensity) of vibration therapy.

In some embodiments, as described herein, the therapy device 300 may be communicatively coupled to a computing device 120. A computing device 120 may include a mobile computing device, a tablet computing device, a laptop computing device, a desktop computing device, etc. The therapy device 300 may couple to the computing device 120 via a wired or wireless connection. Wired connections may be enabled via the I/O interface 110 and may include USB or USB-C. Wireless connections may include Bluetooth, BLE, Wi-Fi, a cellular connection, etc. In some embodiments, the therapy device 300 may be controlled via the computing device. The therapy device 300 may be controlled via a client application operating at the computing device. Control instructions (e.g., setpoints, configurations, etc.) for a therapy device 300 may be input at a computing device and communicated to the therapy device 300. The control instructions may be discrete (e.g., five distinct heating modes, vibration therapy selections, or electrical stimulation intensities) or continuous (e.g., a selectable sliding scale for heating therapy temperature, vibration frequency of vibration therapy, or voltage/current level for electrical stimulation) based on a configuration of the therapy device 300, the therapy (e.g., vibration, heating, or electrical stimulation) provided by the therapy device 300, and/or the computing device controlling the therapy device 300. In some embodiments, control instructions for therapy may be configured to indicate therapy durations and combinations, such that therapies may be applied to a body region 311 in configured sequences. In an example, a user 310 may configure heating therapy and vibration therapy for the first 10 minutes (e.g., 0:00-10:00) of a 30 minute therapy session, electrical stimulation therapy for the second 10 minutes (e.g., 10:00-20:00) of the 30 minute therapy session, and a combination of vibration, heating, and electrical stimulation therapy for the last 10 minutes (e.g., 20:00-30:00) of the 30 minute therapy session. Any suitable combination of vibration, heating, and or electrical stimulation therapy may be configured for any combination of time durations with any combination of ordering for a therapy session.

In some embodiments, as described herein, more than one therapy device 300 may be communicatively coupled to a computing device. Any suitable number of therapy devices 300 may be coupled to a computing device such that the computing device may control the therapy(ies) provided by each of the therapy devices 300 to body regions 311. In some embodiments, each therapy device 300 connected to a computing device may be controlled independently, where each therapy device 300 may be individually configured for vibration, heating, and/or electrical stimulation therapy with configurable setpoints. As described herein, for a plurality of therapy devices 300, any suitable combination of vibration, heating, and or electrical stimulation therapy may be configured for any combination of time durations with any combination of ordering for a therapy session. In some embodiments, each therapy device 300 of connected to a computing device may be controlled in synchronization, such that each therapy device 300 is configured to provide the same therapy for a therapy session. In other embodiments, a plurality of therapy devices 300 may be individually configured for therapy or configured to provide therapy in combination with one or more other therapy devices 300. In an example, for a computing device 120 connected to four therapy devices 300, first and second therapy devices 300 may be individually configured to provide different therapies, while third and fourth therapy devices 300 may be configured to provide a same therapy different from the therapies provided by the first and second therapy devices 300.

In some embodiments, as described herein, the therapy device may be controlled via a client application. The client application may operate at a computing device (e.g., computing device 120) that is communicatively coupled to the therapy device 300. In some cases, control instructions for the therapy device 300 that correspond to one or more of heating therapy, vibration therapy, and electrical stimulation therapy may be provided at the client application, such that the control instructions may be communicated to the therapy device 300 for application. In some cases, feedback information from the therapy device 300 may be communicated to the client application. Feedback information may include one or more of information regarding usage of the therapy pad 200, heating therapy, vibration therapy, and/or electrical stimulation therapy. The client application may include a status dashboard, where therapies administered by the therapy device may be displayed in combination with parameters associated with each of the therapies (e.g., temperature, vibration intensity, electrical pulse intensity, duration, etc.). Feedback information as described herein may be displayed by the status dashboard. In some cases, feedback information may include a power information for the therapy device 300. The power information may include parameters associated with the power supply module 108. A parameter may include a battery level for a battery of the power supply module 108. Battery levels for more than one therapy device 300 may be displayed by the status dashboard based on more than one therapy device 300 being coupled to the client application. In some embodiments, the client application may receive usage information of the therapy device 300 as described herein. Based on the usage information (e.g., duration of use or number of uses for a therapy pad 200), the client application may present an indication to replace the therapy pad 200. The client application may present an indication to purchase one or more additional therapy pads 200 based on the usage information for the therapy device 300 and/or the therapy pad 200. In some embodiments, the client application may be configured (e.g., by a user 310) to automatically purchase one or more therapy pads based on the usage information (e.g., exceeding a usage threshold as described herein) for the therapy device 300.

In some embodiments, via the client application, a user 310 and/or a therapy professional may obtain (e.g., download) control routines for the therapy device 300. The control routines may be available at a cloud computing platform (and/or another type of computing platform), where they may be downloaded by a computing device (e.g., computing device 120). In some cases, the control routines may be included at the client application and/or otherwise accessible via the client application. The computing device may couple to the therapy device 300 and send the control routine to the therapy device via the communication channels described herein. A control routine may include one or more parameters and/or control instructions for heating, vibration, and/or electrical stimulation therapy. Parameters and/or control instructions for the control routine may be configured based on a particular injury and/or recovery. In an example, a control routine for a strained hamstring may be downloaded by the computing device 120 and communicated to the therapy device 300 for application. In some cases, the client application may display one or more control routines based on the number of therapy devices 300 coupled to a computing device. The client application may determine the number of connected therapy devices 300. As a result, control routines may be curated by the client application based on the number of therapy devices connected to the computing device and presented for selection.

In some cases, the client application may include one or more features for a therapy professional and/or a healthcare provider. The client application may be configured to report therapy information to a computing device associated with a therapy professional or healthcare provider. Therapy information may include one or more of the types of therapies applied by connected therapy devices 300, the duration of the therapies, and feedback information from components of the therapy device 300. Feedback information may include information aggregated from temperature sensors 205, accelerometers, and/or pressure sensors. In an example, accelerometer feedback data provided to a therapy professional may enable the therapy professional to analyze a user's response to electrical stimulation therapy, allowing the therapy professional to provide recommendations regarding therapy for a user 310. Feedback information may include information from one or more other suitable sensors and/or components of the therapy device 300. In some cases, via the client application, a therapy professional and/or healthcare provider may recommend control routines. A therapy professional and/or healthcare provider may provide recommended control routines via a computing device including the client application and/or another computing device communicatively coupled to the computing device that includes the client application. Recommended control routines may be provided via the status dashboard of the client application. In some cases, computing devices that include the client application may be communicatively coupled (e.g., by a network connection). In an example, a user computing device that is coupled to a therapy device 300 may receive recommended control routines from the therapy professional computing device based on each computing device including the client application.

Control of Vibration Therapy for a Therapy Device

Referring again to FIGS. 1A, 2A, and 3A-3B, to effectively apply vibration therapy, the therapy device 300 requires a control method to process control instructions for the application of vibration therapy to a body region 311. In some embodiments, as described herein, control instructions may be received at an input device of the therapy device or via a connected computing device (e.g., the computing device 120). The therapy device 300 may include a control method for vibration therapy stored in a memory of the control module 104 and/or the pad control module 204, where the control method may be applied based on received control instructions.

In some embodiments, for vibration therapy, control instructions may include one or more of: a therapy duration and a vibration frequency. A therapy duration may correspond to the total time duration of the vibration therapy. In some embodiments, the duration may correspond to individual time periods within a therapy session such that the vibration therapy is applied to a body region 311. A vibration frequency may correspond to the frequency at which the vibration module 106 vibrates. In some embodiments, the frequency of vibration therapy may be fixed (e.g., not configurable by a user 310). In an example, the vibration frequency of the vibration module 106 may be 98.33 Hz (e.g., 5900 RPM). In other embodiments, the frequency of the vibration therapy may be variable, such that the frequency of the vibration module 106 may be determined based on received control instructions. In an example, vibration therapy may be applied at 90 Hz and 100 Hz during a therapy session. Any suitable combination of therapy duration and vibration frequency may be included in received control instructions for vibration therapy.

In some embodiments, received control instructions for vibration therapy may be applied by the control module 104 or by the pad control module 204 based on a configuration of the therapy device 300. The pad control module 204 may apply received control instructions based on the receiving control instructions from the control module 104 (e.g., via coupled pad interface 112 and I/O channel 214). To apply the received control instructions, the control module 104 (or pad control module 204) may apply a control voltage to the vibration module 106, where the application of the control voltage corresponds to the received control instructions for vibration therapy. In an example, the control module 104 may apply a control voltage to activate the motor of the vibration control module 106, causing the eccentric weight to move and induce vibration at the vibration module 106 and at a body region 311 to which the therapy device 300 is applied.

Control of Heating Therapy for a Therapy Device

Referring again to FIGS. 1A, 2A, and 3A-3B, to effectively apply heating therapy, the therapy device 300 requires a control method to map the temperature generated by the heat generation module 206 to the temperature at a body region 311. As described herein, a temperature sensor 205 (e.g., coupled to the control module 104 or pad control module 204) can be configured to read the temperature at the area the temperature sensor 205 is positioned within the therapy device 300. In some embodiments, as described herein, the temperature sensor 205 may be positioned adjacent or proximal to one or more of: the resistive component 207, the backing layer 208, and the heat spreader 209. In these embodiments, the temperature measured by the temperature sensor 205 may not be representative of the temperature at a body region 311, as multiple elements of the therapy device 300 (e.g., conductors 211, pads 212, adhesive layer 216, etc.) may insulate the resistive component 207 and heat spreader 209 from a body region 311. Further, the body of the user (e.g., the circulatory system) can work to counter the thermal energy applied by the heat generation module 206, resulting in the measured temperature of heat generation module 206 overstating the temperature of a body region 311 during heating therapy. Accordingly, if control parameters for the heat generation module 206 fail to account for this phenomenon, a body region 311 may experience temperatures outside the desired therapeutic temperature ranges for heating. For example, while the temperature sensor 205 may read a temperature of 104° F. during heating therapy applied by the therapy device 300, the actual temperature at a body region 311 may only be 100° F.

In some embodiments, the control module 104 (or pad control module 204) can include instructions for one or more control methods to control and maintain the temperature(s) applied by the therapy device 300. The control methods can be based on the temperature(s) measured by a temperature sensor 205 positioned within the therapy device 300.

In some embodiments, the control module 104 or the pad control module 204 can process control instructions for application to the heat generation module 206. The control instructions may include selection of a desired duration and an intensity level (e.g., a temperature setpoint). A range of intensity levels may be limited to configured therapeutic ranges for heating therapy. In some embodiments, the therapeutic range for heating therapy may be 104° F.-113° F. The intensity levels may be further limited within a therapeutic range. For example, the therapeutic range for heating therapy may be configured to be 104° F.-109° F., as users may indicate discomfort with the therapy device 300 when the temperature at the body region 311 exceeds 109° F. In some embodiments, the intensity level can be a discrete, preconfigured temperature level (e.g., temperature setpoint) selected from a plurality of discrete temperature levels. For example, for heating therapy, the intensity levels available for selection may include: 105° F., 106° F., 107° F., 108° F., and 109° F. Other intensity levels and/or other quantities of intensity levels may be configured. The control module 104 (or pad control module 204) can receive control instructions indicating a selection from the plurality of intensity levels for heating therapy.

In some embodiments, the control instructions may include a manually configured temperature (e.g., temperature setpoint) for therapy. The manually configured temperature may be selected (e.g., by a user) from a range of temperatures, rather than from discrete inputs as described herein. In some embodiments, the range of temperatures available for selection may be segmented into discrete increments (e.g., 0.1° F., 0.5° F., 1° F., etc.). In some embodiments, where the therapy device 300 is configured to receive a manually configured temperature for therapy, the control module 104 (or pad control module 204) can limit the range of temperature setpoints for the heat generation module 106. The control module 104 may limit the range of temperature setpoints to the range of therapeutic temperatures. For example, the control module 104 may be configured to process received temperature inputs within the range of 100° F.-109° F. and discard received temperature inputs that are below 100° F. or above 109° F.

In some embodiments, based on receiving control instructions, the control module 104 can determine a control method. For heating therapy, the control method can function to conserve power (e.g., battery life of the therapy device 300) and maintain safe operating conditions for a user 310. In some embodiments, the control method can define an offset between the temperature measured at the temperature sensor 205 and the resulting temperature at a body region 311. A control method can include a static model to map the temperature measured by the temperature sensor 205 to the resulting temperature at a body region 311 during operation of heat generation module 106.

In some embodiments, a heating control method of the control module 104 can enable the therapy device 300 to apply heating therapy to a body region 311. Heating therapy can include reaching therapeutic heating temperatures at a body region 311. The range of therapeutic cooling temperatures may include 104° F.-113° F. as described herein. In some embodiments, other temperature ranges for heating therapy may be used (e.g., 104° F.-109° F.).

In some embodiments, the heating control method of the control module 104 can be based on a target temperature. The target temperature may be the desired temperature measured by the temperature sensor 205. The temperature measured at the temperature sensor 205 can be representative of the measured temperature at a contact surface (e.g., proximal to a body region 311) of the resistive component 207 or the heat spreader 209. According to the heating control method, the control module 104 can function to drive the resistive component 207 to the target temperature. The control module 104 may drive the resistive component 207 to the target temperature (e.g., temperature setpoint) based on Proportional-Integral-Derivative (PID) control methods. In some embodiments, constants for proportional gain, integral gain, and derivative gain of a PID algorithm can be selected based on combination of power conservation and time to heat a body region 311. Based on the measured temperature of temperature sensor 205 and the target temperature for temperature sensor 205, the control module 104 can apply PID control methods to duty-cycle the control voltage (and corresponding power) applied to the resistive component 207. The control module 104 may duty-cycle the control voltage applied to the resistive component 207 on a range of 0%-100% of the maximum control voltage that can be output by the control module 104. For example, where the maximum control voltage output by the control module 104 is 3.7 V, duty-cycling the control voltage output to 80% would yield an average control voltage output of 2.96 V over a defined time period. In some embodiments, the target temperature can be a function of a selected temperature setpoint for a body region 311, an offset (e.g., a constant offset), and a calibration value. The target temperature for heating therapy by the temperature device 100 can be defined in Table 2 and Equation 3 as follows:

TABLE 1

| Heating Therapy Control Equation (Equation 1) Parameters | |
|---|---|
| Target Temperature | Target temperature measured by a temperature sensor |
| Body Temperature | Selected temperature setpoint for a body region |
| Offset | Constant function of expected temperature difference between temperature measured by temperature sensor and temperature of a body region |
| Calibration | Calibration constant determined during manufacturing |

$$\text{Target Temperature}=\text{Body Temperature}+\text{Offset}+\text{Calibration} \quad \text{Equation 1}$$

Equation 1 as described above may be defined in ° F. In some embodiments, alternate units of temperature (e.g., ° C.) can be used for Equation 1. As described herein, the "Target Temperature" described in Table 1 and Equation 1 can be the target temperature measured by the temperature sensor 205. For example, according to Equation 1, the control module 104 can apply a control voltage to the resistive component 207, heating the resistive component 207 such that the measured temperature at the temperature sensor 205 is the "Target Temperature".

In some embodiments, the "Body Temperature" constant described in Table 1 and Equation 1 can be a temperature setpoint for the therapy device 300 included in received control instructions. For example, based on receiving control instructions from a computing device 120 indicating a temperature setpoint of 105° F., the "Body Temperature" constant can be configured to 105 in Equation 1.

In some embodiments, the "Offset" constant described in Table 1 and Equation 1 can be a constant function that represents the expected temperature difference between the measured temperature of the temperature sensor 205 (e.g., the temperature of the resistive component 207) and the expected temperature at a body region 311 during operation of the therapy device 300. The "Offset" constant can account for a body region's resistance (e.g., through blood circulation, sweating, etc.) to temperature change over time, as well as the difference in temperature at a body region 311 and at the TEC 128 due to thermal buffering effects from elements of the therapy device 300 (e.g., the conductor 211, the pad 212, the adhesive layer 216, etc.). In some embodiments, the "Offset" constant may be equal to 10° F. Alternate "Offset" constant values (e.g., 5° F., 10° F., etc.) may be defined to represent the relationship between the measured temperature at the temperature sensor 205 and the actual temperature of a body region 311.

In some embodiments, the "Calibration" constant described in Table 1 and Equation 1 can be a temperature measurement constant defined for the therapy device 300. The "Calibration" constant may be configured individually for each therapy device 300. In some embodiments, the "Calibration" constant may be configured based on quality control test during manufacturing of the therapy device 300. The "Calibration" constant may function to account for manufacturing defects in the therapy device 300 such that a difference between the temperature measured at the temperature sensor 205 and the temperature of a body region 311 vary beyond an expected temperature range (e.g., 5° F., 7° F., 10° F., etc.). As an example, if the expected temperature difference between the temperature measured by the temperature sensor 205 and the temperature of a body region 311 during heating therapy is 8° F. and the measured temperature difference is 6° F., the "Calibration" constant may be configured to 2° F. As another example, if the expected temperature difference is 8° F. and the measured temperature difference is 11° F., the "Calibration" constant may be configured to −3° F. By including the "Calibration" constant, the control module 104 can heat the resistive component 207 to the (approximate) temperature setpoint included in the received control instructions based on measurements from the temperature sensor 205.

In some embodiments, the control module 104 can apply a control voltage to the heat generation module 206 (and resistive component 207) to initiate heating therapy based on receiving control instructions. The control instructions can include a temperature setpoint for the therapy device 300, where the temperature setpoint can be selected from one or more discrete, preconfigured temperature levels or manually configured as described herein. Based on receiving control instructions including a temperature setpoint, the control module 104 can apply a control voltage to the resistive component 207 according to the "Target Temperature" of Equation 1. As an example, for a "Body Temperature" of 105° F., an "Offset" of 8° F., and "Calibration" constant of −3° F., the control module 104 would target a measured temperature of 110° F. at the temperature sensor 205. The control module 104 can duty-cycle the control voltage applied to the resistive component 207 based on difference between the measured temperature at the temperature sensor 205 and the "Target Temperature" for the temperature sensor 205. The control module 104 can duty-cycle the control voltage based on PID control techniques to minimize the difference between the measured temperature at the temperature sensor 205 and the "Target Temperature" for the temperature sensor 205 as described herein. For example, as the measured temperature approaches the "Target Temperature", the control module 104 can duty-cycle the control voltage such that the average control voltage is 70% of the maximum control voltage, enabling the temperature therapy device 100 to conserve power (e.g., battery life for the power supply module 108) and approach the "Target Temperature" without significantly surpassing the "Target Temperature". As the measured temperature of the temperature sensor 205 approaches and/or reaches the "Target Temperature", the control module 104 can duty-cycle the control voltage such that the measured temperature at the temperature sensor 205 stabilizes about the "Target Temperature". Based on stabilizing the measured temperature, the control module 104 can enable heating therapy at approximately the selected temperature setpoint.

In some embodiments, control of the heat generation module 106 may be based on the electrical stimulation therapy provided by the electrical stimulation module(s) 210. The "Target Temperature" may be changed from the value(s) indicated by the control instructions based on a configuration of control instructions for the electrical stimulation module(s) 210. Based control instructions for one or more of a pulse frequency, a pulse width, and a pulse intensity for the electrical stimulation module(s) 210, the control module 104 may increase or reduce the value for the "Target Temperature". The control module 104 may include one or more thresholds for pulse frequency, pulse width, and pulse intensity that may cause the control module 104 to increase or reduce the "Target Temperature" measured by the temperature sensor 205. In an example, the control module 104 may reduce the "Target Temperature" measured by the temperature sensor 205 by 2° F. based on exceeding a threshold pulse frequency for the electrical stimulation module(s) 210. The control module 104 may duty cycle the control voltage applied to the resistive component 207 as described herein to automatically increase or reduce the temperature setpoint or "Target Temperature" based on the control instructions for electrical stimulation therapy. The control module 104 may modify control of heating therapy provided by the heat generation module 206 based on feedback from the electrical stimulation therapy as described herein. In some embodiments, the pad control module 204 may perform the operations as described herein.

Control of Electrical Stimulation Therapy for a Therapy Device

Referring again to FIGS. 1A, 2A, and 3A-3B, to effectively apply electrical stimulation therapy, the therapy device 300 requires a control method for controlling the electrical stimulation modules 210 when applied at a body region 311 of a user 310. As described herein, each electrical stimulation may include a conductor 211 and an pad 212, where the conductor 211 transports an electrical signal to the pad 212. The pad 212 may be applied to a body region 311 of a user 310 (in combination with the adhesive layer 216), such that electrical stimulation therapy may be applied to the body region 311 via one or more electrical pulses.

In some embodiments, as described herein, control instructions may be received at an input device of the therapy device or via a connected computing device (e.g., the computing device 120). The therapy device 300 may include a control method for electrical stimulation stored in a memory of the control module 104 and/or the pad control module 204, where the control method may be applied based on received control instructions.

In some embodiments, for electrical stimulation therapy, control instructions may include one or more of: a therapy duration, a pulse frequency, a pulse width, and a pulse intensity. A therapy duration may correspond to the total time duration of the electrical stimulation therapy. The therapy duration may be configured in the received control instructions. A pulse frequency may correspond to the frequency of the applied electrical pulses of the electrical stimulation therapy, where the therapy device 300 is configured to provide electrical pulses to body region 311 via the electrical stimulation module(s) 210. In some embodiments, the pulse frequency for electrical stimulation therapy may be fixed (e.g., not configurable by a user 310). In other embodiments, the pulse frequency may be variable, such that the pulse frequency may be indicated by received control instructions. In some embodiments, the frequency of electrical pulses may range from 0.1 Hz to 150 Hz based on a configuration of the therapy device 300. A pulse width may correspond to the time duration of each electrical pulse output by the electrical stimulation module(s) 210. In some embodiments, the pulse width for electrical stimulation therapy may be fixed (e.g., not configurable by a user 310). In other embodiments, the pulse width may be variable, such that the pulse width may indicated by received control instructions. A pulse intensity may correspond to the magnitude (e.g., current, voltage, power, etc.) of an electrical pulse. In some embodiments, the pulse intensity may be fixed, such that a user 310 may not configure the pulse intensity. In other embodiments, the intensity may be variable, such that a user 310 or another individual (e.g., a therapy professional) may select a pulse intensity for electrical stimulation therapy in the control instructions for the therapy device 300. Any suitable combination of therapy duration, pulse frequency, pulse width, and pulse intensity may be included in received control instructions for electrical stimulation therapy.

In some embodiments, received control instructions for electrical stimulation therapy may be applied by the control module 104 or by the pad control module 204 based on a configuration of the therapy device 300. The pad control module 204 may apply received control instructions based on the receiving control instructions from the control module 104 (e.g., via coupled pad interface 112 and I/O channel 214). To apply the received control instructions to the therapy device 300, the control module 104 (or pad control module 204) may apply a control voltage (or pulses of a control voltage) to each (or a subset) of the electrical stimulation modules 210, where the application of the control voltage corresponds to the received control instructions for electrical stimulation therapy. In an example, the control module 104 may apply a control voltage to each conductor 211, where each conductor 211 may transport the control voltage to each corresponding pad 212, where each pad 212 may provide electrical stimulation therapy to a body region 311 of a user 310 to which the therapy device 300 is applied.

In some embodiments, the electrical stimulation module (s) 210 may be controlled by a feedback electrical stimulation control method of the control module 104. The feedback electrical stimulation control method may use feedback information obtained by the control module to control one or more of the therapy duration, pulse frequency, pulse width, and/or pulse intensity for electrical stimulation therapy. Feedback information may include accelerometer data and/or pressure data provided by the therapy device 300 (e.g., by one or more accelerometers and/or pressure sensors). Accelerometer data and/or pressure data may be mapped to muscle twitch corresponding to electrical stimulation therapy as described herein. The electrical stimulation control method may configure one or more of the parameters for electrical stimulation therapy to achieve a target feedback measurement. A feedback measurement may be an accelerometer measurement and/or a pressure measurement as described herein. The control module 104 may compare measured parameter information (e.g., from an accelerometer, pressure sensor, or one or more of both types of sensor)

to target parameter information. Based on a difference between the measured parameter information and the target parameter information, the control module 104 may configure pulse frequency, pulse width, and/or pulse intensity for each of the electrical stimulation module(s) 210. In some cases, each electrical stimulation module 210 may be configured for an individual target parameter measurement. Based on the positioning of the sensors (e.g., accelerometers and/or pressure sensors) within the therapy device 300, each electrical stimulation module 210 may be controlled by the control module 104 to achieve the target parameter measurement. In an example, the control module 104 may configure the pulse intensity of pulses output by a pair of electrical stimulation modules 210*a* and 210*b* to achieve a configured target accelerometer data measurement indicative of muscle twitch at a body region 311.

In some embodiments, feedback control of the electrical stimulation module(s) 210 may be based on the heating therapy provided by the heat generation module 206. One or more of a pulse frequency, a pulse width, and a pulse intensity may be changed from the value(s) indicated by the control instructions based on a configuration of control instructions for the heat generation module 206 (e.g., a temperature setpoint or the "Target Temperature"). Based on control instructions for a temperature setpoint (or another parameter of heating therapy) of the heat generation module 206, the control module 104 may increase or reduce the value(s) for one or more of the pulse frequency, pulse width, and pulse intensity of electrical stimulation therapy. The control module 104 may include one or more thresholds for the temperature setpoint or the "Target Temperature" that may cause the control module 104 to increase or reduce one or more of the pulse frequency, pulse width, and pulse intensity. In an example, the control module 104 may reduce the pulse frequency of electrical stimulation therapy provided by the electrical stimulation module(s) 210 based on exceeding a threshold temperature setpoint of 106° F. for heating therapy. The control module 104 may duty cycle the control voltage applied to conductors 211 to modify the electrical stimulation therapy as described herein, such that the electrical stimulation therapy may be automatically changed based on the control instructions for heating therapy. The control module 104 may modify control of electrical stimulation therapy provided by the electrical stimulation module(s) 210 based on feedback from the heating therapy as described herein. In some embodiments, the pad control module 204 may perform the operations as described herein.

Control Method for a Therapy Device

Figure 5:
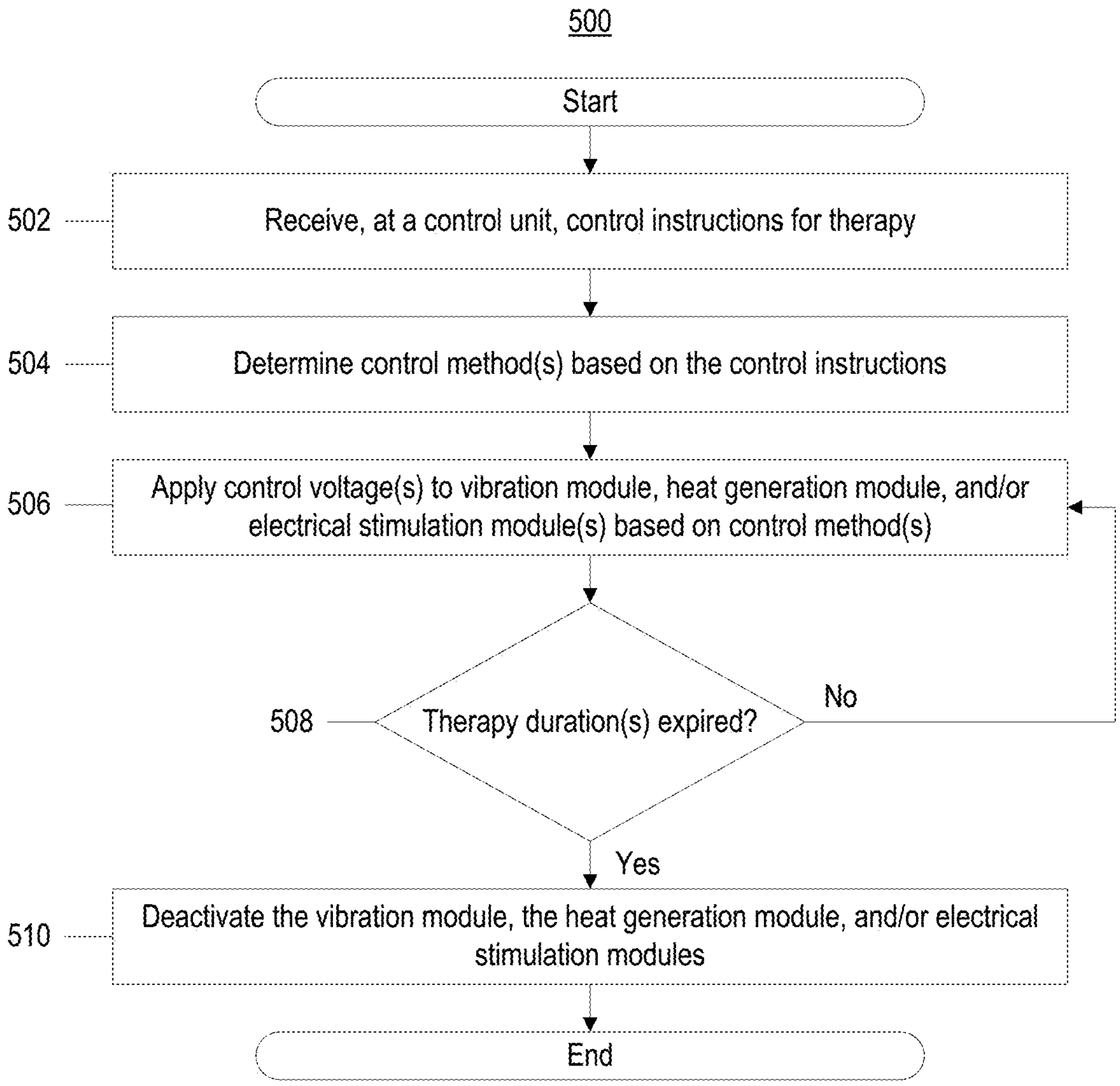
FIG. 5 illustrates an exemplary flowchart for a method of controlling an exemplary therapy device, in accordance with some embodiments.

To apply vibration, heating, and/or electrical stimulation therapy as described herein, the therapy device 300 can execute a control method. Referring to FIG. 5, a flowchart for a control method 500 of a therapy device (e.g., therapy device 300) is presented, according to some embodiments. A control module (e.g., control module 104) or a pad control module (e.g., pad control module 204) can apply the temperature control method 500 as described herein to a vibration module (e.g., vibration module 106), a heat generation module (e.g., heat generation module 206), and/or electrical stimulation module(s) (e.g., electrical stimulation module(s) 210).

At step 502, a control unit (e.g., control unit 100) can receive control instructions. As described herein, the control unit can receive control instructions from one or more input devices of the control unit or from a computing device (e.g., the computing device 120) connected to the control unit. In some embodiments, the control instructions may be received by a control module (e.g., control module 104). The durations (e.g., schedules) described herein for each of vibration, heating, and electrical stimulation therapy may include more than one duration, such that a particular type of therapy may be alternately enabled (e.g., activated) and disabled (e.g., deactivated) during the total therapy duration. The control instructions can include a duration for vibration therapy and a vibration frequency for a vibration module (e.g., vibration module 106). The control instructions can include a duration for heating therapy and a temperature for heating therapy at a body region (e.g., body region 311). The control instructions can include a duration for electrical stimulation therapy, as well as a pulse frequency, a pulse width, and a pulse intensity for electrical pulses provided by electrical stimulation module(s) (e.g., electrical stimulation module(s) 210). In some embodiments, the control instructions can include a combination of the above described parameters for vibration, heating, and/or electrical stimulation therapy. The control instructions may include one or more sequences and/or routines for applying the combination of vibration, heating, and/or electrical stimulation therapy, such that specific therapies may be activated and/or deactivated during the duration of the therapy, while the above described parameters may be configured to vary during the duration of the therapy. Accordingly, any suitable combination of vibration, heating, and/or electrical stimulation therapy may be indicated by the received control instructions.

At step 504, the control unit can determine the control method(s) for a therapy device (e.g., therapy device 300) based on the received control instructions. The control module may determine the control method(s) based on whether vibration, heating, and/or electrical stimulation therapy were indicated by the received control instructions. The control module may determine a vibration control method based on receiving control instructions indicating a selection of vibration therapy. The control instructions indicating a selection of vibration therapy may indicate a duration for vibration therapy and a vibration frequency for the vibration module as described herein. The control module may determine a heating control method based on receiving control instructions indicating a selection of heating therapy. The control instructions indicating a selection of heating therapy can include a duration for heating therapy and a temperature for heating therapy at a body region as described herein. The control module may determine a target temperature for the heat generation module (e.g., heat generation module 206) and an included resistive component (e.g., resistive component 207) based on the received temperature for heating therapy, where the heating control method may drive the resistive component to the target temperature as described herein. The control module may determine a electrical stimulation control method based on receiving control instructions indicating a selection of electrical stimulation therapy. The control instructions indicating a selection of vibration therapy may indicate a duration for electrical stimulation therapy, as well as a pulse frequency, a pulse width, and/or a pulse intensity for electrical pulses provided by the electrical stimulation module(s).

At step 506, the control module can apply one or more control voltage(s) to the vibration module, the heat generation module, and/or the electrical stimulation module(s) according to the determined control method(s). Each control voltage may be applied for a duration indicated by each corresponding control method.

At step 508, the control module can determine whether each of the therapy durations indicated each of the control methods have elapsed to disable the application of the control voltage(s). The control module may determine to apply control voltage(s) to a first subset of the vibration module, the heat generation module, and/or the electrical stimulation module(s), while determining to deactivate a second subset of the vibration module 106, the heat generation module, and/or the electrical stimulation module(s) at step 508.

At step 510, the control module may deactivate the vibration module, the heat generation module, and/or the electrical stimulation module(s) based on the corresponding expired therapy duration(s). Disabling corresponding control voltages may deactivate the vibration module, the heat generation module, and/or the electrical stimulation module(s). Based on determining one or more therapy durations have not expired, the control module 104 may continue to apply control voltages to the corresponding elements of the therapy device at step 506 as described herein.

Computer Systems

Figure 6:
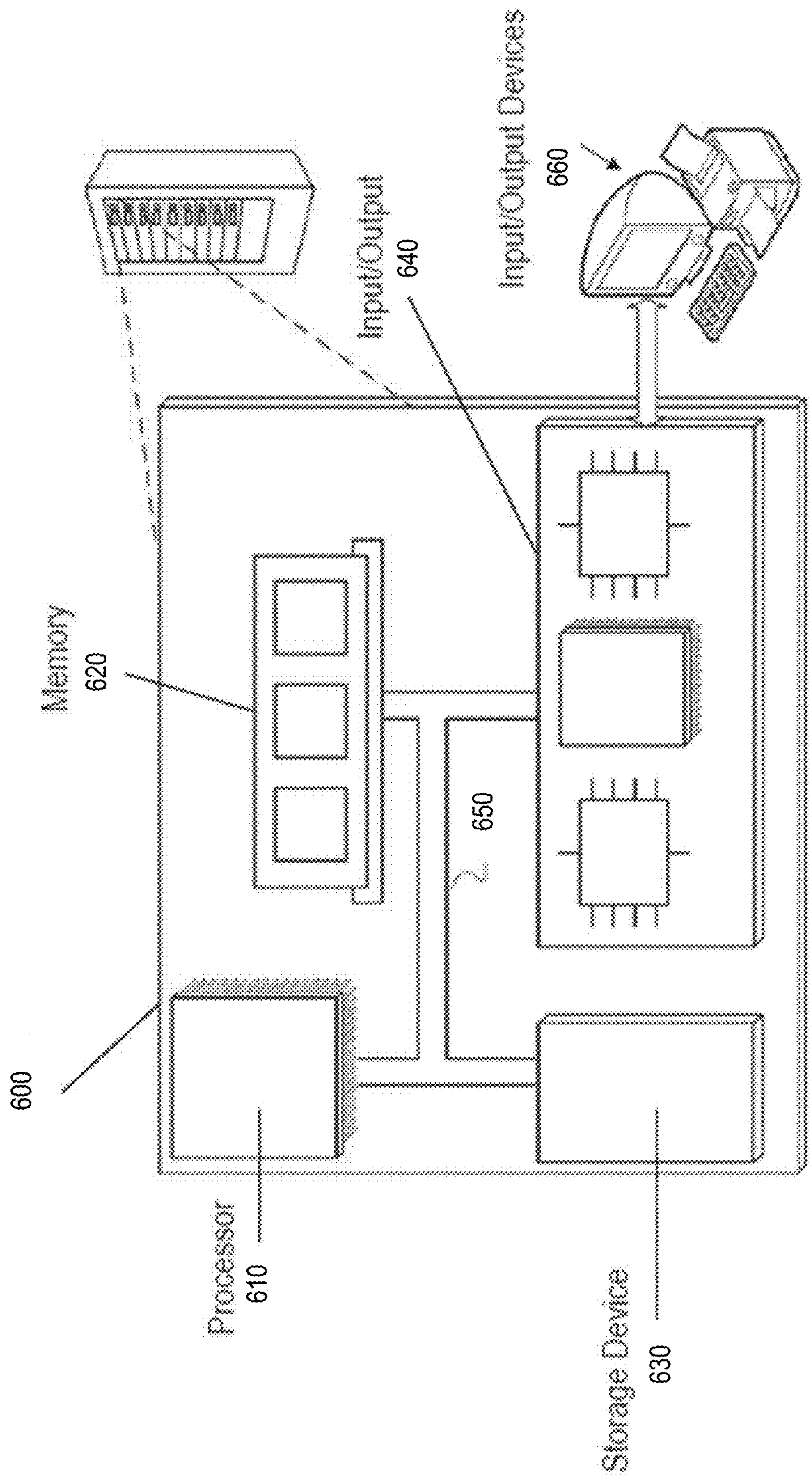
FIG. 6 illustrates a block diagram of an example computer system, according to some embodiments.

FIG. 6 is a block diagram of an example computer system 600 that may be used in implementing the technology described in this document. General-purpose computers, network appliances, mobile devices, or other electronic systems may also include at least portions of the system 600. The system 600 includes a processor 610, a memory 620, a storage device 630, and an input/output device 640. Each of the components 610, 620, 630, and 640 may be interconnected, for example, using a system bus 650. The processor 610 is capable of processing instructions for execution within the system 600. In some implementations, the processor 610 is a single-threaded processor. In some implementations, the processor 610 is a multi-threaded processor. The processor 610 is capable of processing instructions stored in the memory 620 or on the storage device 630.

The memory 620 stores information within the system 600. In some implementations, the memory 620 is a non-transitory computer-readable medium. In some implementations, the memory 620 is a volatile memory unit. In some implementations, the memory 620 is a non-volatile memory unit.

The storage device 630 is capable of providing mass storage for the system 600. In some implementations, the storage device 630 is a non-transitory computer-readable medium. In various different implementations, the storage device 630 may include, for example, a hard disk device, an optical disk device, a solid-date drive, a flash drive, or some other large capacity storage device. For example, the storage device may store long-term data (e.g., database data, file system data, etc.). The input/output device 640 provides input/output operations for the system 600. In some implementations, the input/output device 640 may include one or more of a network interface devices, e.g., an Ethernet card, a serial communication device, e.g., an RS-232 port, and/or a wireless interface device, e.g., an 602.11 card, a 3G wireless modem, or a 4G wireless modem. In some implementations, the input/output device may include driver devices configured to receive input data and send output data to other input/output devices, e.g., keyboard, printer and display devices 660. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 630 may be implemented in a distributed way over a network, for example as a server farm or a set of widely distributed servers, or may be implemented in a single computing device.

Although an example processing system has been described in FIG. 6, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

Measurements, sizes, amounts, and the like may be presented herein in a range format. The description in range format is provided merely for convenience and brevity and should not be construed as an inflexible limitation on the scope of the invention. Accordingly, the description of a range should be considered to have specifically disclosed all the possible subranges as well as individual numerical values within that range. For example, description of a range such as 1-20 meters should be considered to have specifically disclosed subranges such as 1 meter, 2 meters, 1-2 meters, less than 2 meters, 10-11 meters, 10-12 meters, 10-13 meters, 10-14 meters, 11-12 meters, 11-13 meters, etc.

Furthermore, connections between components or systems within the figures are not intended to be limited to direct connections. Rather, data or signals between these components may be modified, re-formatted, or otherwise changed by intermediary components. Also, additional or fewer connections may be used. The terms "coupled," "connected," or "communicatively coupled" shall be understood to include direct connections, indirect connections through one or more intermediary devices, wireless connections, and so forth.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A therapy device, comprising:

a therapy pad comprising:

an adhesive layer configured to adhere to a skin surface of a user;

a heat generation module having a resistive component and thermally coupled to a heat spreader configured to distribute thermal energy generated by the resistive component across an area of the heat spreader;

a temperature sensor coupled to the heat generation module and configured to measure a temperature at the heat generation module;

a thermal insulator layer, wherein the heat generation module and the temperature sensor are both positioned between the thermal insulator layer and the adhesive layer; and a fabric top layer adjacent a top surface of the thermal insulation layer;

a control unit coupled to the therapy pad, wherein the control unit is configured to provide temperature therapy to the skin surface of the user and provide vibration therapy to the skin surface of the user.

2. The therapy device of claim 1, wherein the control unit is further configured to:

receive one or more control instructions for controlling the temperature therapy and/or the vibration therapy.

3. The therapy device of claim 2, wherein the control unit comprises a wireless connection and wherein the control unit is further configured to receive the one or more control instructions via the wireless connection.

4. The therapy device of claim 2, wherein the control unit comprises one or more input devices and wherein the control unit is further configured to receive the one or more control instructions via the one or more input devices.

5. The therapy device of claim 1, wherein the control unit further comprises:

a vibration module configured to provide the vibration therapy, wherein the vibration module comprises a motor; and a power supply module configured to provide electrical power to the vibration module and the heat generation module.

6. The therapy device of claim 1, further comprising:
a coupling mechanism, wherein the therapy pad and the control unit are configured to removably couple via the coupling mechanism.

7. The therapy device of claim 6, wherein the coupling mechanism comprises one or more magnets.

8. The therapy device of claim 6, wherein the control unit further comprises the coupling mechanism and wherein the therapy pad further comprises:
a coupling connector configured to removably couple to the coupling mechanism.

9. The therapy device of claim 1, wherein the adhesive layer is disposed on the heat spreader.

10. The therapy device of claim 1, wherein the control unit is further configured to provide electrical stimulation therapy to the skin surface of the user.

11. The therapy device of claim 10, wherein the therapy pad further comprises:
one or more electrical stimulation modules configured to provide the electrical stimulation therapy, where each electrical stimulation module comprises a conductor and an electrical stimulation pad.

12. A therapy pad, comprising:
a coupling connector configured to removably couple a control unit;
a thermal insulator layer;
a heat generation module having a resistive component and thermally coupled to a heat spreader configured to distribute thermal energy generated by the resistive component across an area of the heat spreader;
a temperature sensor coupled to the heat generation module and configured to measure a temperature at the heat generation module;
an adhesive layer coupled to the heat spreader, wherein the heat generation module and the temperature sensor are both positioned between the thermal insulator layer and the adhesive layer; and
a fabric top layer adjacent a top surface of the thermal insulation layer.

13. A method for controlling a therapy device, comprising:
receiving, by a control unit of the therapy device, one or more control instructions for controlling a temperature therapy and/or a vibration therapy;
sending, from the control unit to a therapy pad of the therapy device, a subset of the one or more control instructions, wherein the control unit is coupled to the therapy pad, and wherein the therapy pad comprises:
an adhesive layer configured to adhere the therapy pad to a skin surface of a user;
a heat generation module having a resistive component and thermally coupled to a heat spreader configured to distribute thermal energy generated by the resistive component across an area of the heat spreader;
a temperature sensor coupled to the heat generation module and configured to measure a temperature at the heat generation module;
a thermal insulator layer, wherein the heat generation module and the temperature sensor are both positioned between the thermal insulator layer and the adhesive layer; and
a fabric top layer adjacent a top surface of the thermal insulation layer;
receiving, by the therapy pad from the control unit, the subset of the one or more control instructions; and
providing, by the control unit via the therapy pad, the temperature therapy and/or the vibration therapy to the skin surface of the user based on the one or more control instructions.

14. The therapy device of claim 1, wherein the heat generation module further comprises a backing layer comprising one or more channels, and wherein the resistive component is provided on the backing layer.

15. The therapy device of claim 1, wherein the thermal insulator layer is configured to insulate the control unit from the thermal energy generated by the resistive component.

16. The therapy device of claim 1, wherein the therapy pad further comprises a coupling connector configured to removably couple to the control unit, and wherein:
the coupling connector is positioned above the thermal insulator layer,
the thermal insulator layer is positioned between the heat generation module and the coupling connector,
the heat generation module is positioned between the adhesive layer and the thermal insulator layer,
the temperature sensor is positioned between the heat spreader and the thermal insulator layer, and
the adhesive layer is positioned below the heat generation module.

* * * * *